United States Patent
Ratan et al.

(10) Patent No.: US 11,963,939 B2
(45) Date of Patent: *Apr. 23, 2024

(54) USE OF N-ACETYLCYSTEINE TO TREAT CENTRAL NERVOUS SYSTEM DISORDERS

(71) Applicants: Neuronasal, Inc., Wexford, PA (US); Burke Neurological Institute, White Plains, NY (US)

(72) Inventors: Rajiv R. Ratan, Scarsdale, NY (US); Saravanan Karuppagounder, White Plains, NY (US); Thomas I. Bradshaw, Wynnewood, PA (US)

(73) Assignees: Neuronasal, Inc., Wexford, PA (US); Burke Neurological Institute, White Plains, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/154,550

(22) Filed: Jan. 13, 2023

(65) Prior Publication Data
US 2023/0414548 A1 Dec. 28, 2023

Related U.S. Application Data

(63) Continuation of application No. 16/700,588, filed on Dec. 2, 2019, now Pat. No. 11,660,278, which is a continuation of application No. 15/968,355, filed on May 1, 2018, now abandoned.

(60) Provisional application No. 62/500,381, filed on May 2, 2017.

(51) Int. Cl.
| | |
|---|---|
| A61K 31/198 | (2006.01) |
| A61K 9/00 | (2006.01) |
| A61K 31/05 | (2006.01) |
| A61K 31/145 | (2006.01) |
| A61P 25/18 | (2006.01) |
| A61P 25/24 | (2006.01) |

(52) U.S. Cl.
CPC .......... *A61K 31/198* (2013.01); *A61K 9/0043* (2013.01); *A61K 31/05* (2013.01); *A61K 31/145* (2013.01); *A61P 25/18* (2018.01); *A61P 25/24* (2018.01)

(58) Field of Classification Search
CPC .... A61K 31/05; A61K 31/145; A61K 31/198; A61K 9/0043; A61K 31/215; A61K 31/22; A61K 31/221; A61P 25/18; A61P 25/24
See application file for complete search history.

(56) References Cited

U.S. PATENT DOCUMENTS

| 7,618,615 B2 | 11/2009 | Frey, II et al. |
| 11,612,642 B2 | 3/2023 | Kole et al. |
| 11,660,278 B2 | 5/2023 | Ratan et al. |
| 2012/0190731 A1 * | 7/2012 | Messina ............. A61P 1/06 514/249 |
| 2013/0005666 A1 | 1/2013 | Ratan et al. |
| 2014/0187640 A1 | 7/2014 | Goldstein |
| 2015/0038586 A1 | 2/2015 | Goldstein |
| 2018/0344678 A1 | 12/2018 | Ratan et al. |
| 2021/0128509 A1 | 5/2021 | Greene |

FOREIGN PATENT DOCUMENTS

| FR | 2594694 A1 | 8/1987 | |
| WO | 2006060027 A2 | 6/2006 | |
| WO | WO-2012030664 A1 * | 3/2012 | ........... A61K 31/137 |
| WO | 2015112724 A1 | 7/2015 | |
| WO | 2015120038 A1 | 8/2015 | |
| WO | 2018204393 A1 | 11/2018 | |
| WO | 2019084543 A1 | 5/2019 | |

OTHER PUBLICATIONS

Hanson et al. ((BMC Neurosci. 2008; 9(Suppl 3): S5 pp. 1-4), (Year: 2008).*
Ehrick et al. (Sterile Product Development. 2013; 6: 99-144) (Year: 2013).*
Mischley et al (NPJ Parkinsons Dis. 2016; 2: 16002, Published online Feb. 25, 2016, 1-6 pages). (Year: 2016).*
Adair et al., Controlled trial of Nacetylcysteine for patients with probable Alzheimer's disease, 2001, Neuroplogy; 51; 1515-1517.
Aoyama, K., Glutathione in the brain, 2021, Int J Mol Sci. 55: 5010.
Baker et al., The Origin and Neuronal Function of In Vivo Nonsynaptic Glutamate, 2002, The Journal of Neuroscience, 22(20): 9134-9141.
Benes et al., Protection from oxidative and electrophilic stress in the Gsta4-null mouse heart, 2014, Cardiovasc Toxicol, 13(4), 1-19.
Berk et al., The promise of N-acetylcysteine in neuropsychiatry, Trends in Pharm. Sci, 2013; vol. 34, No. 3, 167-177.
Bhatti et al., Systematic Review of Human and Animal Studies Examining the Efficacy and Safety of N-Acetylcysteine (NAC) and N-Acetylcysteine Amide (NACA) in Traumatic Brain Injury: Impact on Neurofunctional Outcome and biomarkers of Oxidative Stress and Inflammation, frontiers in Neurology, 2018, vol. 8, p. 1-14.
Bitter et al., Nasal drug delivery in humans, 2011, Curr Probl Dermatol. 40: 20-35.
Bjorklund et al., The glutathione system in Parkinson's disease and its progression, 2021, Neurosci Biobehav Rev. 120: 470-478.
Borgstrom et al., Pharmacokinetics of N-acetylcysteine in man, 1986, Eur J Clin Pharmacol. 31: 217-222.
Carmichael et al., Genomic profiles of damage and protection in human intracerebral hemorrhage, 2008, Journal of Cerebral Blood Flow & Metabolism, 28, 1860-1875.
Chang et al., Swollen Nuclei Signal from the Grave, 2016; Cell 165; 1051-1052.

(Continued)

*Primary Examiner* — Jean P Cornet
(74) *Attorney, Agent, or Firm* — Frost Brown Todd LLP

(57) ABSTRACT

The present disclosure describes methods of treating a central nervous system condition associated with oxidative stress using a 5-lipoxigenase activating protein (FLAP) inhibitor, for example, N-acetylcysteine or nordihydroguaiaretic acid. The present disclosure also describes methods of treating a central nervous system condition with N-acetylcysteine and a second therapeutic agent such as prostaglandin E2.

22 Claims, 39 Drawing Sheets

(56) References Cited

OTHER PUBLICATIONS

Chauhan et al., Brain Uptake of Neurotherapeutics after Intranasal versus Intraperitoneal Delivery in Mice, J. Neurol. Neurosurg, 2015, vol. 2 (1), p. 1-20.
Chuang et al., Botanical Polyphenols Mitigate Microglial Activation and Microglia-Induced Neurotoxicity: Role of Cytosolic Phospholipase A2, 2016, Neuromol Med, 18; 415-425.
Clark et al., Oral N-Acetyl-Cysteine Attenuates Loss of Dopaminergic Terminals in a-Synuclein Overexpressing Mice, 2010, PLoS One, vol. 5 (8) 1-10.
Corps, Kara N et al., "Inflammation and neuroprotection in traumatic brain injury." JAMA neurology vol. 72,3 (2015): 355-62. doi: 10.1001/jamaneurol.2014.3558.
Crowe et al., Mechanism of intranasal drug delivery directly to the brain, Life Sciences, 2018, vol. 195, p. 44-52.
De Lizarrondo et al., Potent Thrombolytic Effect of N-Acetylcysteine on Arterial Thrombi, Circulation, 2017; 136; 646-660.
Dekhuijzen et al., The role for N-acetylcysteine in the management of COPD, 2006, International Journal of COPD; 1(2) 99-106.
Dringen et al., Glutathion pathways in the brain, 2003, Biol Chem. 384: 505-516.
Eakin, Katharine et al., "Efficacy of N-acetyl cysteine in traumatic brain injury." PloS one vol. 9,4 e90617, Apr. 16, 2014, doi:10.1371/journal.pone.0090617.
Echeverria et al., Expression of Prostaglandin E2 Synthases in Mouse Postnatal Cortical Neurons, 2005, Ann. NY Acad. Sci. 1053: 460-471.
Enyedi et al., The Cell Nucleus Serves as a Mechanotransducer of Tissue Damage-Induced Inflammation, 2016, Cell; 165; 1160-1170.
Funk et al., Prostaglandins and Leukotrienes: Advances in Eicosanoid Biology, 2001, Science 294, 1871-1875.
Ganti et al., Int J Emerg Med. 2014; 7 (Year: 2014).
Giza, Christopher C and David A Hovda, "The new neurometabolic cascade of concussion." Neurosurgery vol. 75 Suppl 4,0 4 (2014): S24-33. doi:10.1227/NEU.0000000000000505.
Gong et al., Inducible cyclooxygenase-2 expression after experimental intracerebral hemorrhage, 2001, Elsevier; Brain Research 901; 38-46.
Green et al., Oral and Intravenous Acetylcysteine for Treatment of Acetaminophen Toxicity: A Systematic Review and Meta-analysis, 2013, Western Journal of Emergency Medicine; vol. 14(3), 218-226.
Grossetete et al., Matrix metalloproteinase inhibition facilitates cell death in intracerebral hemorrhage in mouse, 2008, Journal of Cerebral Blood Flow & Metabolism, vol. 28, 752-763.
Guo, J et al., N-acetylcysteine treatment following spinal cord trauma reduces neural tissue damage and improves locomotor function in mice, 2015, Molecular Medicine Reports, vol. 12: 37-44.
Hanley et al., Safety and efficacy of minimally invasive surgery plus recombinant tissue plasminogen activator in intracerebral haemorrhage evacuation (MISTIE): a randomised, phase 2 trial, 2016, Lancet Neurol, 15(12) 1228-1237.
Hatakeyama et al., Deferoxamine reduces neuronal death and hematoma lysis after intracerebral hemorrhage in aged rats, 2013, Transl Stroke Res., 4(5) 1-15.
Hicdonmez, T et al, "Neuroprotective effects of N-acetylcysteine on experimental closed head trauma in rats", Neurochem Res. Apr. 2006, 31(4):473-81. Epub May 9, 2006.
Higdon et al., Hemin causes mitochondrial dysfunction in endothelial cells through promoting lipid peroxidation: the protective role of autophagy, 2012, Am J Physiol Heart Circ Physiol; 302: H1394-H1409.
Hijioka et al., Inhibition of Leukotriene B4 Action Mitigates Intracerebral Hemorrhage-Associated Pathological Events in Mice, 2016, J Pharmacol Exp Ther, 3 (60): 399-408.
Hoffer et al., Amelioration of Acute Sequelae of Blast Induced Mild Traumatic Brain Injury by N-Acetyl Cysteine: A Double-Blind, Placebo Controlled Study, PLOS One, 2013, vol. 8, p. 1-10.
Holdiness, M.R., Clinical pharmacokinetics of N-acetylcysteine, 1991, Clin Pharmacokinet. 20: 123-134.
Holmay, Mary J et al., N-acetylcysteine Boosts Brain and Blood Glutathione in Gaucher and Parkinson's Diseases, Clin Neuropharmacol., 2013, vol. 36 (4), p. 103-106.
Thomas, Shane; International Search Report and Written Opinion of the International Searching Authority, issued in International Application No. PCT/US2018/030499; Jul. 16, 2018; 11 pages.
Jogani et al., Recent Patents Review on Intranasal Administration for CNS Drug Delivery, Recent Patents on Drug Delivery & Formulation, 2008, vol. 2, pp. 25-40.
Karuppagounder et al., N-Acetylcysteine Targets 5 Lipoxygenase-Derived, Toxic Lipids and Can Synergize With Prostaglandin E2 to Inhibit Ferroptosis and Improve Outcomes Following Hemorrhagic Stroke in Mice, 2018, Ann Neurol, 84: 854-872.
Karuppagounder et al., Therapeutic targeting of oxygen-sensing prolyl hydroxylases abrogates ATF4-dependent neuronal death and improves outcomes after brain hemorrhage in several rodent models, 2016, Sci Transl Med., 1-37.
Kawoos et al., Protective Effect of N-Acetylcysteine Amide on Blast-Induced Increase in Intracranial Pressure in Rats, Frontiers in Neurology, 2017, vol. 8, p. 2-8.
Keller et al., Intranasal drug delivery: opportunities and toxicologic challenges during drug development, 2022, Drug Deliv Trasl Res. 12: 735-757.
Khan et al., Administration of N-Acetylcysteine after Focal Cerebral Ischemia Protects Brain and Reduces Inflammation in a Rat Model of Experimental Stroke, 2004, Journal of Neuroscience Research, 76:519-527.
Kim et al., A Promoter polymorphism (rs17222919,-1316T/G) of ALOX5AP is associated with intracerebral hemorrhage in Korean population, 2011, Elsevier; 82, 115-120.
Labib et al., The Safety and Feasibility of Image-Guided BrainPath-Mediated Transsulcul Hematoma Evacuation: A Multicenter Study, 2017, NeuroSurgery, vol. 80(4), 515-524.
Li et al., Inhibition of neuronal ferroptosis protects hemorrhagic brain, 2017, JCI insight, pp. 1-19.
Lin et al., Suppression of Steady-state, but not Stimulus-induced NFk B Activity Inhibits Alphavirus-induced Apoptosis, 1998, The Journal of Cell Biology, vol. 141 (7); 1479-1487.
Lin et al., Thiol Agents and Bcl-2 Identify an Alphavirus-induced Apoptotic Pathway That Requires Activation of the Transcription Factor NF-kappa B, 1995; The Journal of Cell Biology, vol. 131; 1149-1161.
Lopez-Erauskin et al., Antioxidants Halt Axonal Degeneration in a Mouse Model of X-Adrenoleukodystrophy, 2011, Ann Neurol; 70: 84-92.
Maclellan et al., The Influence of Hypothermia on Outcome After Intracerebral Hemorrhage in Rats, 2006, Stroke; 37: 1266-1270.
Majgainya et al., Novel Approach for Nose-to-Brain Drug Delivery Bypassing Blood Brain Barrier by Pressurized Olfactory Delivery Device, J. App Pharm, 2015, vol. 7 (3), pp. 148-163.
Markoutsa, E. et al., Redox potential sensitive N-acetyl cysteine-prodrug nanoparticles inhibit the activation of microglia and improve neuronal survival, 2018, Mol Pharm, vol. 14(5): 1591-1600.
McCrea, M et al., "Incidence, clinical course, and predictors of prolonged recovery time following sport-related concussion in high school and college athletes", J Int Neuropsychol Soc., Jan. 2013, 19(1):22-33. doi: 10.1017/S1355617712000872. Epub Oct. 12, 2012.
McCullough et al., Neuroprotective Function of the PGE2 EP2 Receptor in Cerebral Ischemia, The Journal of Neuroscience, 2004, 24(1): 257-268.
McInnes, Kerry et al. "Mild Traumatic Brain Injury (mTBI) and chronic cognitive impairment: A scoping review." PloS One vol. 12,4 e0174847. Apr. 11, 2017, doi: 10.1371/journal.pone.0174847.
Milne et al., The Cyclopentenone Product of Lipid Peroxidation, 15-A2t-Isoprostane, Is Efficiently Metabolized by HepG2 Cells via Conjugation with Glutathione, 2004, Chem. Res. Toxicol, vol. 17, 17-25.
Mischley et al., Central nervous system uptake of intranasal glutathione in Parkinson's disease, Parkinson's Disease Foundation, 2016, p. 1-6.
Mohan et al., Neuroprotective Role of Prostaglandin PGE2 EP2 Receptor in Hemin-mediated Toxicity, 2015, Neurotoxicology, vol. 46, 53-59.

(56) References Cited

OTHER PUBLICATIONS

Monti et al., N-Acetyl Cysteine May Support Dopamine Neurons in Parkinson's Disease: Preliminary Clinical and Cell Line Data, 2016, PloS One, vol. 10, 1-15.

Nisenbaum, Eric J et al. "The presence and role of iron in mild traumatic brain injury: an imaging perspective." Journal of neurotrauma vol. 31,4 (2014): 301-7. doi:10.1089/neu.2013.3102.

North et al., PGE2-regulated wnt signaling and N-acetylcysteine are synergistically hepatoprotective in zebrafish acetaminophen injury, 2010, PNAS, vol. 107(40), 17315-17320.

Porta et al., L-2-Oxothiazolidine-4-Carboxylic Acid, a Cysteine Prodrug: Pharmacokinetics and Effects on Thiols in Plasma and Lymphocytes in Human, 1991, The Journal of Pharmacology and Experimental Therapeutics, vol. 257 (1) 331-334.

Qureshi et al., Intra-Arterial Recanalization Techniques for Patients 80 Years or Older with Acute Ischemic Stroke: Pooled Analysis from 4 Prospective Studies, 2009, AJNR, 1184-1189.

Ratan et al., Oxidative Stress Induces Apoptosis in Embryonic Cortical Neurons, 1994, J. Neurochem, vol. 62(1) 366-379.

Ratan et al., Macromolecular Synthesis Inhibitors Prevent Oxidative Stree-induced Apoptosis in Embryonic Cortical Neurons by Shunting Cysteine from Protein Synthesis to Glutathione, 1994, The journal of Neuroscience, 14(7); pp. 4385-4392.

Reyes et al., Neuronal Glutathione Content and Antioxidant Capacity can be Normalized In Situ by N-acetyl Cysteine Concentrations Attained in Human Cerebrospinal Fluid, 2015, Neurotherapeutics, vol. 13: 217-225.

Robinson et al., Using Enzyme Assays to Evaluate the Structure and Bioactivity of Sponge-Derived Meroterpenes, 2009, J Nat Prod.; 72(10): 1857-1863.

Rosa et al., N-acetylcysteine replenishes glutathione in HIV infection, 2000, European Journal of Clinical Investigation, 30, 915-929.

Roth, Theodore L et al. "Transcranial amelioration of inflammation and cell death after brain injury." Nature vol. 505,7482 (2014): 223-8. doi: 10.1038/nature12808.

Samuelsson et al., The Discovery of the Leukotrienes, 2000, Am J Respir Crit Care Med, vol. 161, S2-S6.

Samuni, Y et al., 2013, The chemistry and biological activities of N-acetylcysteine, Biochem Biophys Acta, 1830(8), 4117-4129.

Selvaraj et al., Nose to brain transport pathways an overview: potential of nanostructured lipid carriers in nose to brain targeting, Artificial Cells, Nanomedicine, and Biotechnology, 2018, vol. 46 (8), p. 1-9.

Shahripour, Rb et al., N-acetylcysteine (NAC) in neurological disorders: mechanisms of action and therapeutic opportunities, 2014, Brain and Behavior, vol. 4(2): 108-122.

Smirnova et al., Development of Neh2-Luciferase Reporter and Its Application for High Throughput Screening and Real-Time Monitoring of Nrf2 Activators, 2011, Chemistry & Biology 18, 752-765.

Sun et al., N-acetylcysteine attenuates reactive-oxygen-species-mediated endoplasmic reticulum stress during liver ischemia-reperfusion injury, World J Gastroenterol, Nov. 7, 2014; 20(41), 15289-15298.

Teleflex LLC, MAD Nasal, User Guide: Intranasal Mucosal Atomization Device, 2017.

Tuite P., Magnetic resonance imaging as a potential biomarker for Parkinson's disease, 2016, Transl Res. 174: 4-16.

Van Asch et al., Early Intracerebral Hematoma Expansion After Aneurysmal Rupture, 2010, Stroke, vol. 41k, 2592-2595.

Wang et al., Chitosan-NAC Nanoparticles as a Vehicle for Nasal Absorption Enhancement of Insulin, Journal of Biomedical Materials Research Part B: Applied Biomaterials, Wiley InterScience, 2007, p. 150-161.

Williamson et al., Rehabilitation Augments Hematoma Clearance and Attenuates Oxidative Injury and Ion Dyshomeostasis After Brain Hemorrhage, 2017, Stroke, vol. 48, 195-203.

Wright et al., N-Acetylcysteine improves mitochondrial function and ameliorates behavioral deficits in the R6/1 mouse model of Huntington's disease, 2014, Nature, vol. 5, 1-10.

Xiong, et al., Effect of yV-Acetylcysteine on Mitochondrial Function Following Traumatic Brain Injury in Rats, 1999, Journal of Neurotrauma, vol. 16 (11) 1067-1082.

Zhang, H. et al., A Pharmacogenetic Discovery: Cystamine Protects Against Haloperidol-Induced Toxicity and Ischemic Brain Injury, 2016, Genetics, vol. 203, 599-609.

Zille et al., Neuronal Death After Hemorrhagic Stroke In Vitro and In Vivo Shares Features of Ferroptosis and Necroptosis, 2017, Stroke, vol. 48, 1033-1043.

Schwellenbach; Alleged traumatic brain injury research misconduct investigated by the Pentagon; Jul. 30, 2010; 3 pages.

Allnutt, Sarah; Extended European Search Report issued in European Patent Application No. 18793795.8; May 20, 2021; 8 pages.

\* cited by examiner

A.

B.

A.

B.

A.

B.

C.

A.

B.

USE OF N-ACETYLCYSTEINE TO TREAT CENTRAL NERVOUS SYSTEM DISORDERS

CROSS REFERENCE

This application is a continuation of U.S. application Ser. No. 16/700,588 filed Dec. 2, 2019, which is a continuation of U.S. application Ser. No. 15/968,355 filed May 1, 2018, which claims the benefit under 35 U.S.C. § 119 of U.S. Provisional Patent Application 62/500,381, filed May 2, 2017, the contents of each of which is incorporated herein by reference in its entirety.

GOVERNMENT RIGHTS

This invention was made with government support under P01 NIA AG014930, Project 1 to RRR by the National Institutes of Health. The government has certain rights in the invention.

BACKGROUND

Hemorrhagic stroke, defined as bleeding within the brain parenchyma, accounts for 13-15% of all stroke cases. Nearly half of afflicted patients die, and survivors commonly experience long-term disability. Identification of novel targets to treat hemorrhagic stroke is an important unmet public need.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the disclosure provides a method of treating a central nervous system condition comprising administering to a subject in need thereof a therapeutically-effective amount of a 5-lipoxygenase activating protein (FLAP) inhibitor.

BRIEF DESCRIPTION OF THE FIGURES

FIG. 13 PANEL B shows total iron levels in the cortex, intrahematomal, and perihematomal regions of the brain of collagenase-infused ICH mice with or without NAC treatment. The graph shows mean±SEM.

FIG. 14 PANEL B shows that combinations of non-protective concentrations of NAC, TRO, or LA failed to synergize in preventing hemin-induced ferroptosis in primary cortical neurons. The graphs show mean±SEM.

FIG. 15 PANEL B shows that BW-4AC was effective in inhibiting ALOX5. FIG. 15 PANEL C shows that NAC was not effective at inhibiting ALOX5.

FIG. 18 PANEL B shows the increase in ALOX-derived LTB4 after induction of ICH in rats. FIG. 18 PANEL C shows the increase in ALOX-derived LTE4 after induction of ICH in rats.

FIG. 21 PANEL B shows that hemin increased ALOX AP levels in a time-dependent manner, while NAC blocked the expression of ALOX AP in primary cortical neurons.

FIG. 34 PANEL B shows prostaglandin E2 ($PGE_2$) levels as determined by GC/MS analysis in sham injected mice and in collagenase-infused ICH mice over time following collagenase injection. FIG. 34 PANEL C shows prostaglandin D2 ($PGD_2$) levels as determined by GC/MS analysis in sham-injected mice and in collagenase-infused ICH mice over time following collagenase injection. FIG. 34 PANEL D shows prostaglandin $F_2$ ($PGF_2$) levels as determined by GC/MS analysis in sham-injected mice and in collagenase-infused ICH mice over time following collagenase injection. FIG. 34 PANEL E shows 6-keto-prostaglandin $F_2$ (6-keto $PGF_2$) levels as determined by GC/MS analysis in sham-injected mice and in collagenase-infused ICH mice over time following collagenase injection.

FIG. 39 PANEL B shows behavioral analysis results for the adhesive tape removal task in saline-injected mice, untreated collagenase-injected ICH mice, and collagenase-injected ICH mice treated with NAC, $PGE_2$, or NAC+$PGE_2$.

DETAILED DESCRIPTION

Figure 1:
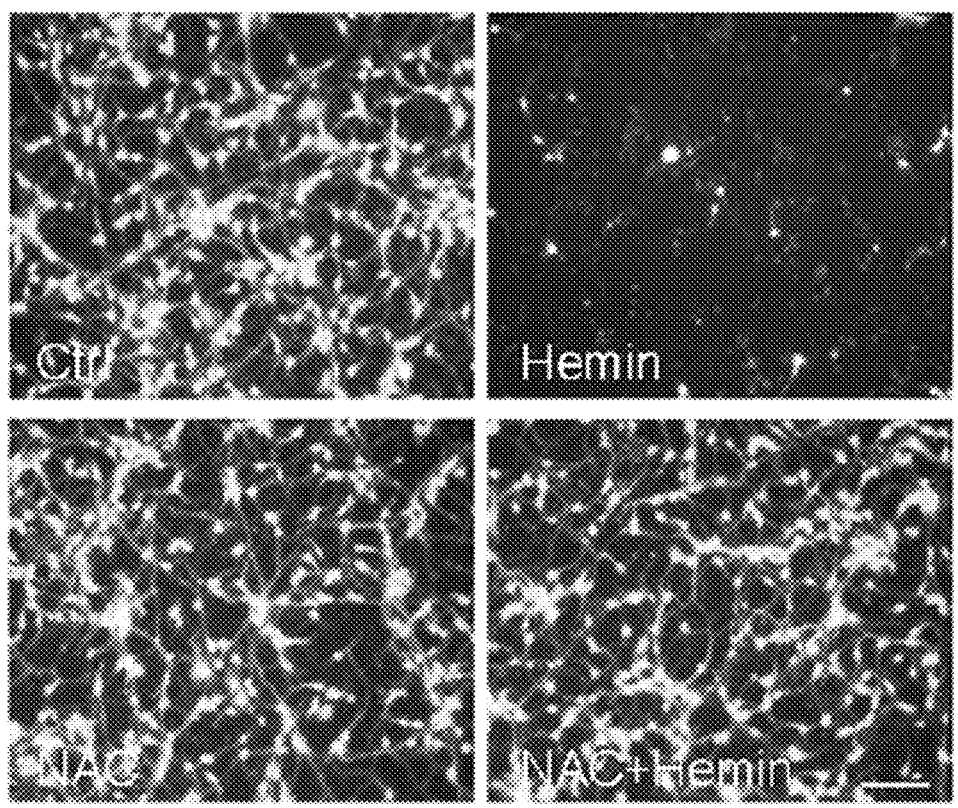
FIG. 1 shows representative live/dead images of primary cortical neurons 24 hours (h) after treatment with saline (Ctrl), NAC (1 mM), Hemin (100 µM) and Hemin (100 µM)+NAC (1 mM). Scale bars: 100 µm.

Intracerebral hemorrhage (ICH), also known as cerebral bleeding, is a type of intracranial bleed that occurs within the brain tissue or ventricles. Symptoms can include headache, one-sided weakness, vomiting, seizures, fever, decreased level of consciousness, and neck stiffness. Symptoms often worsen over time. ICH is also a stroke subtype that accounts for 13-15% of all stroke cases, and remains a significant cause of mortality and morbidity. Nearly half of the afflicted patients die, and survivors commonly suffer from long-term disability. Identification of novel targets to treat hemorrhagic stroke is an unmet public need.

Causes of ICH include brain trauma, aneurysms, arteriovenous malformations, and brain tumors. The largest risk factors for spontaneous bleeding are high blood pressure and amyloidosis. Other risk factors for ICH include alcoholism, low cholesterol, blood thinners, and cocaine use. Diagnosis is typically conducted by computed tomography angiography (CTA) and magnetic resonance angiography (MRA) scans.

Stoichiometric use of antioxidants, such as vitamin E and Cerovive® (NXY-059), for stroke treatment has been decreasing because the concentrations required for the antioxidants is relatively high compared to therapeutic agents that work catalytically. For stoichiometric antioxidants, one molecule of antioxidant is used to neutralize one oxidant. If the concentration of an antioxidant drug that reaches the CNS is below the level of injury-induced oxidant production, the antioxidant agent will be ineffective.

The present disclosure describes the use of a catalytic amount of a compound to treat a neurological disorder. In some embodiments, the disclosure describes the use of a catalytic amount of NAC to treat a CNS condition. In some embodiments, NAC can prevent cell death. In some embodiments, NAC can enhance functional recovery from a CNS condition. The present disclosure also describes the use of NAC to treat a CNS condition by targeting ALOX5-derived reactive lipid species to mediate neuroprotective effects. In some embodiments, the disclosure describes the use of NAC and a second therapeutic agent to treat a CNS condition. The present disclosure also describes a method of treating a CNS condition by administering a 5-lipoxygenase activating protein (FLAP) inhibitor.

Indications

The present disclosure describes the use of a compound to treat a neurological disorder. A neurological disorder is any disorder of the nervous system. Structural, biochemical, or electrical abnormalities in the brain, spinal cord, or other nerves can result in a range of symptoms. Examples of symptoms that arise from neurological disorders include paralysis, muscle weakness, poor coordination, loss of sensation, seizures, confusion, pain, and altered levels of consciousness.

The present disclosure describes the use of a compound to treat a neurological disorder. In some embodiments, the disclosure describes the use of a compound to treat brain damage, such as cerebral lobe (e.g., basal ganglia, cerebellum, or the brainstem) damage, frontal lobe damage, parietal lobe damage, temporal lobe damage, or occipital lobe damage. In some embodiments, the present disclosure describes the use of a compound to treat brain dysfunction according to type: aphasia (language), dysgraphia (writing), dysarthria (speech), apraxia (patterns of sequences of movements), agnosia (identifying things or people), or amnesia (memory). In some embodiments the present disclosure describes the use of a compound to treat spinal cord disorders, peripheral neuropathy and other peripheral nervous system disorders, cranial nerve disorders (e.g., Trigeminal neuralgia), autonomic nervous system disorders (e.g., dysautonomia, Multiple System Atrophy), or seizure disorders (i.e., epilepsy).

In some embodiments, the disclosure describes the use of a compound to treat a movement disorder of the central and peripheral nervous system, such as Essential tremor, Amyotrophic lateral sclerosis, Tourette's syndrome, Multiple Sclerosis, and various types of peripheral neuropathy. In some embodiments, the disclosure describes the use of a compound to treat sleep disorders (e.g., narcolepsy), migraines and other types of headaches, or central neuropathy. In some embodiments, the disclosure describes the use of a compound to treat a neuropsychiatric illness, such as attention deficit hyperactivity disorder, autism, or obsessive compulsive disorder.

The methods of the disclosure can be used to treat a CNS condition. CNS disorders are a group of neurological disorders that affect the structure or function of the brain or spinal cord, which collectively form the CNS. The disclosure describes use of a compound to treat a CNS disorder caused by traumatic brain injury, concussion, post-concussion syndrome, infections, degeneration (e.g., degenerative spinal disorders), structural defects (e.g., anencephaly, hypospadias, spina bifida, microgyria, polymicrogyria, bilateral frontoparietal polymicrogyria, or pachgyria), tumors, autoimmune disorders, or stroke. In some embodiments, the disclosure describes the use of a compound to treat traumatic brain injury. In some embodiments, the disclosure describes the use of a compound to treat subarachnoid hemorrhage. In some embodiments, the CNS condition associated with oxidative stress treated by a method of the invention is stroke (e.g., intracerebral hemorrhage or other hemorrhagic stroke), brain injury (e.g., traumatic brain injury such as concussion), spinal cord injury, a neurodegenerative condition (e.g., Alzheimer's disease, Parkinson's disease, Huntington's disease, multi system atrophy, multiple sclerosis, amyolotrophic lateral sclerosis, cerebral ischemia, seizure disorders, schizophrenia, Friedreich's ataxia, progressive supranuclear palsy, prions, Down's syndrome, ataxia, tardive dyskinesia, or aging), or a neuropsychiatric condition (e.g., schizophrenia, bipolar disorder, or depression). In some embodiments, the disclosure describes the use of a compound to treat concussion. In some embodiments, the disclosure describes the use of a compound to treat post-concussion syndrome.

In some embodiments, the disclosure describes the use of a compound to treat stroke. Stroke is a medical condition in which poor blood flow to the brain results in cell death. The two main types of strokes are ischemic stroke resulting from a lack of blood flow, and hemorrhagic stroke resulting from bleeding. Signs and symptoms of a stroke may include an inability to move or feel on one side of the body, problems understanding or speaking, and a loss of vision to one side. In some embodiments, the disclosure describes the use of a compound to treat hemorrhagic stroke. In some embodiments, the disclosure describes the use of a compound to treat ICH stroke.

Mechanism of Action

In some embodiments, NAC prevents cell death or enhances functional recovery by inhibiting one target. In some embodiments, the present disclosure describes the use of a compound to treat a CNS condition by targeting nuclear arachidonate 5-lipoxygenase (ALOX5)-derived reactive lipid species. Following ICH, 5-lipoxygenase-derived lipids are important for cell death. Transcriptomic analyses of brain tissue obtained from human ICH patients have identified an increased expression of mRNAs encoding ALOX5 and 5-LOX-activating protein (ALOX5AP) FLAP. In some embodiments, NAC is administered to a subject, which targets nuclear ALOX5-derived reactive lipid species in mediating neuroprotective effects in vitro and in vivo.

In some embodiments, NAC prevents cell death or enhances functional recovery by inhibiting more than one target. In some embodiments, NAC prevents cell death or enhances functional recovery by targeting nuclear ALOX5-derived reactive lipid species and products of COX-2 metabolism. In some embodiments, NAC or a compound of the disclosure inhibits FLAP.

Compounds of the Invention

N-acetylcysteine (NAC) is a glutathione prodrug that is used to treat acetaminophen-induced liver failure and to loosen thick mucus individuals with cystic fibrosis or chronic obstructive pulmonary disease. NAC can be taken intravenously, by mouth, or inhaled as a mist. Common side effects of NAC include nausea and vomiting when NAC is administered orally. NAC can also cause skin redness and itching and a non-immune type of anaphylaxis. NAC has multiple putative targets of action, and NAC has poor penetration into the CNS. NAC has been reported to cause nausea and vomiting, induce bronchospasm, slow blood clotting, and induce neurotoxicity in a dose-dependent manner, which can be problematic for patients with hemorrhagic stroke.

The present disclosure describes the use of at least one compound or a pharmaceutically-acceptable salt thereof to treat a CNS condition. In some embodiments, the disclosure describes the use of NAC or a pharmaceutically-acceptable salt thereof to treat a CNS condition. In some embodiments, the disclosure describes the use of NAC amide or a pharmaceutically-acceptable salt thereof to treat a CNS condition. In some embodiments, the disclosure describes the use of a NAC prodrug or a pharmaceutically-acceptable salt thereof to treat a CNS condition. In some embodiments, the disclosure describes the use of cysteine or a pharmaceutically-acceptable salt thereof to treat a CNS condition.

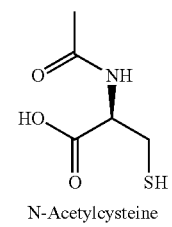

N-Acetylcysteine

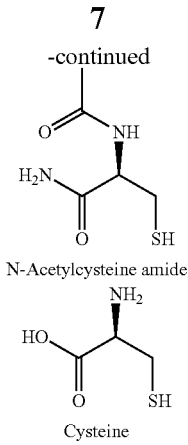

N-Acetylcysteine amide

Cysteine

Cystamine is a disulfide-containing antioxidant compound. In some embodiments, the disclosure describes the use of cystamine or a pharmaceutically-acceptable salt thereof to treat a CNS condition.

Nordihydroguaiaretic acid (NDGA) is an antioxidant compound found in the creosote bush (*Larrea tridentata*). In some embodiments, the disclosure describes the use of NDGA or a pharmaceutically-acceptable salt thereof to treat a CNS condition.

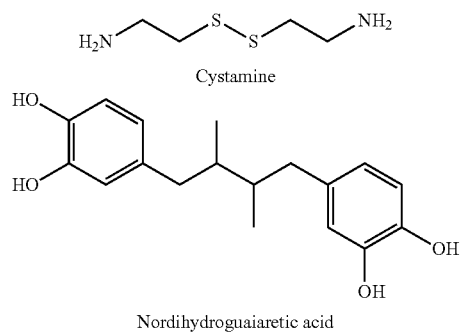

Cystamine

Nordihydroguaiaretic acid

Purity of Compounds of the Invention

Any compound of the disclosure can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutical Composition of the Invention

The present disclosure describes pharmaceutical compositions comprising NAC, which can be administered to a subject to treat a CNS condition. A pharmaceutical composition of the disclosure can be a combination of any pharmaceutical compound described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration. A pharmaceutical composition can be administered in a local manner, for example, via injection of the compound directly into an organ, optionally in a depot or sustained release formulation or implant.

A compound of the disclosure can be administered intranasally, and can be formulated into a variety of inhalable compositions, such as solutions, suspensions, vapors, or powders. Intranasal pharmaceutical compositions can contain solubilizers, stabilizers, tonicity enhancing agents, buffers and preservatives.

In practicing the methods of treatment or use provided herein, therapeutically-effective amounts of a compound described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compound used, and other factors. A compound of the disclosure can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. A formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions of the disclosure can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising a compound described herein include formulating a compound with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow a compound to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), each of which is incorporated by reference in its entirety.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of a compound. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues.

Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Modes of Administration

A compound of the disclosure can be administered as an intranasal spray. In some embodiments, a compound can be packaged in a pressurized aerosol container with suitable propellants and adjuvants. In some embodiments, the propellants are hydrocarbon propellants, such as propane, butane, or isobutene. In some embodiments, aerosol formulations can include other ingredients, such as co-solvents, stabilizers, surfactants, antioxidants, lubricants, and pH adjusters. The aerosol formulations can be administered using a metered dose inhaler.

A compound of the disclosure can be administered as a sprayable powder. In some embodiments, a compound can be administered as an inhalable dry powder. In some embodiments, the powder formulation can include pharmaceutically acceptable excipients, such as monosaccharides (e.g., glucose, arabinose), disaccharides (e.g., lactose, saccharose, maltose), oligosaccharides or polysaccharides (e.g., dextrane), polyalcohols (e.g., sorbitol, mannitol, xylitol), salts (e.g., sodium chloride, calcium carbonate), or any combination thereof. In some embodiments, a compound can be administered as a solution, suspension, or a dry powder. In some embodiments, a compound can be administered in a non-pressurized form using a nebulizer or an atomizer.

Delivery of a compound of the disclosure as an intranasal pharmaceutical composition results in lower systemic drug exposure and fewer side effects. In some embodiments, lower systemic drug exposure can lower the risk of bleeding, gastrointestinal side effects, liver toxicity, fluid retention or edema, neutropenia or leukopenia, anemia, or infection. In some embodiments, lower systemic drug exposure can lower the risk of gastrointestinal side effects, such as nausea, vomiting, or diarrhea.

A compound of the disclosure can be administered directly to the nasal cavity. In some embodiments, a compound can be administered intranasally in the form of a vapor or drops. In some embodiments, a compound can be administered using a intranasal delivery device, such as a rhinyle catheter, multi-dose dropper, unit-dose pipette, or vapor inhaler. In some embodiments, a compound can be delivered using a squeeze bottle, multi-dose metered-dose spray pump, single or duo-dose spray pump, or a bidirectional multi-dose spray pump. In some embodiments, a compound can be delivered using an atomizer. In some embodiments, a compound can be delivered using a nebulizer.

In some embodiments, a compound can be administered intranasally in the form of a powder. In some embodiments, a compound can be delivered using mechanical powder sprayer, breath actuated inhaler, or a insufflator. In some embodiments, a compound can be delivered using a mechanical powder spray device. In some embodiments, a compound can be delivered using a multi-dose powder inhaler, single or duo-dose capsule inhaler, or a nasal inhaler. In some embodiments, a compound can be delivered using a insufflator, or a breath-powered bi-directional delivery system.

In some embodiments, a compound of the disclosure can be administered to a subject using minimally invasive surgery. In some embodiments, a compound of the disclosure can be administered to a subject using BrainPath®, a transsulcal system for subcortical surgery. In some embodiments, a compound of the disclosure can be administered to a subject as a combinatory neuroprotective treatment that is delivered directly to a hematoma site.

Multiple therapeutic agents can be administered in any order or simultaneously. In some embodiments, a compound of the disclosure can be administered in combination with, before, or after a second agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

The disclosure describes the administration of NAC or a NAC derivative to treat a CNS condition. In some embodiments, NAC or a NAC derivative id administered with a second therapeutic agent to treat a CNS condition. In some embodiments, NAC is administered to a subject with a prostaglandin to treat a CNS condition. In some embodiments, NAC is administered with prostaglandin E2 ($PGE_2$) to treat a CNS condition. In some embodiments, co-administration of NAC and PGE₂ allows the therapeutic dose of NAC and PGE₂ to be lower than when NAC and PGE₂ are administered alone.

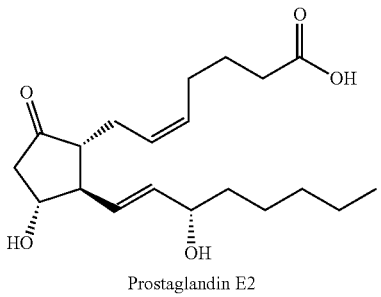 [SMILES: CCCCC[C@H](O)/C=C/[C@H]1[C@H](O)CC(=O)[C@@H]1C/C=C\CCCC(=O)O]

Prostaglandin E2

Dosing

Pharmaceutical compositions described herein can be in unit dosage forms suitable for single administration of precise dosages. In unit dosage form, the formulation is divided into unit doses containing appropriate quantities of one or more compound. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be administered to a subject in a composition in a range of from, about 1 mg/kg to about 5 mg/kg, about 1 mg/kg to about 10 mg/kg, about 1 mg/kg to about 25 mg/kg, about 10 mg/kg to about 50 mg/kg, about 10 mg/kg to about 75 mg/kg, about 10 mg/kg to about 100 mg/kg, about 50 mg/kg to about 125 mg/kg, about 50 mg/kg to about 150 mg/kg, about 50 mg/kg to about 175 mg/kg, about 50 mg/kg to about 200 mg/kg, about 100 mg/kg to about 225 mg/kg, about 100 mg/kg to about 250 mg/kg, about 100 mg/kg to about 275 mg/kg, about 100 mg/kg to about 300 mg/kg, about 150 mg/kg to about 325 mg/kg, about 150 mg/kg to about 350 mg/kg, about 150 mg/kg to about 375 mg/kg, about 150 mg/kg to about 400 mg/kg, about 250 mg/kg to about 425 mg/kg, about 250 mg/kg to about 450 mg/kg, or about 250 mg/kg to about 500 mg/kg.

In some embodiments, a compound of the disclosure can be administered to a subject in a composition in an amount of about 1 mg/kg to about 10 mg/kg. In some embodiments, a compound of the disclosure can be administered to a subject in a composition in an amount of about 1-50 mg/kg. In some embodiments, a compound of the disclosure can be administered to a subject in a composition in an amount of about 1-75 mg/kg. In some embodiments, a compound of the disclosure can be administered to a subject in a composition in an amount of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

Clinical Assessment Tools

Several tools can be utilized to diagnose and assess the clinical and neuropsychological features of CNS conditions, for example, mild traumatic brain injury. In some embodiments, standard physical and neurological examinations, and neuropsychometric batteries and scales with broader applicability (e.g., Glasgow coma scale) can be used to diagnose and assess a subject with a CNS condition.

Post-concussion symptom score (PCSS): The PCSS score consists of 22 items that evaluate symptoms on a 7-point scale. 0 correlates to no symptoms, and 6 correlates to severe symptoms. PCSS scores have utility for subjects ages 11 and above in identifying individuals with clinically-diagnosed concussion, and in predicting prolonged recovery. PCSS scores have also demonstrated test-retest reliability.

Graded symptom checklist (GSC): The GSC consists of 16 items scored on a 7-point scale. The GSC scale is applicable to subjects ages 13 and above, and incorporates a three-factor structure (cognitive, somatic, and neurobehavioral). The GSC scale has demonstrated internal validity, test-retest reliability, and convergent validity with respect to balance and cognitive performance.

Standardized concussion assessment tool (SCAT): SCAT is a standardized tool that is used by healthcare professionals, and incorporates other assessment scales, such as GCS, Maddocks questions for memory assessment, PCSS, and other neurological and cognitive tests.

Immediate post-concussion assessment and cognitive testing (ImPACT): ImPACT is a computerized test battery with 3 components, such as demographic data, neuropsychological testing, and PCSS. ImPACT has the advantage of including assessments of cognition (e.g., attention, processing speed, impulsivity, and reaction time). In a combination with a scale for mTBI symptoms, ImPACT has a sensitivity of 81.9%, and a specificity of 89.4%. ImPACT is not subject to substantial practice effects.

King-Devick Scale: The King-Devick scale is a brief test administered acutely following head injury in which the subject must read patterns of letters and numbers on test cards. The King-Devick scale assess language, attention, and eye movements, all of which can be impaired in a CNS condition, for example, concussion. The test-retest reliability of the King-Devick scale over a period of 1-2 years compares is comparable to other standard assessment methods.

Biomarkers and imaging: Electrophysiological techniques, imaging techniques, and blood tests can be used to assess the CNS condition of a subject. Event-related potentials (EPRs) can be used to evaluate computer-processed electroencephalogram (EEG) signals time-locked to a perpetual or cognitive task. In some embodiments, computed tomography (CT) and magnetic resonance imaging (MRI) can be used to diagnose or track the progress of a CNS condition. In some embodiments, diffusion tensor imaging can be used to diagnose or track the progression of a CNS condition.

In some embodiments, MRI can be used to determine the levels of metabolites in the brain and assess the progress of a CNS disease. In some embodiments, MM can be used to quantify metabolite levels in the range of µmoles/g, such as N-acetylaspartate, lactate, glutamate, gamma-aminobutyric acid, and glutathione.

EXAMPLES

Example 1: Materials and Methods

Animals: C57BL/6 and pregnant CD1 mice of 10-12 weeks were used. The animals were housed in a pathogen-free facility on a 12-hour light/dark cycle, and were provided ad libitum access to food and water, unless stated otherwise. 171 adult male Sprague Dawley rates (~350 g-400 g) were used in the studies to examine the effects of NAC. 40 mg/kg or 75 mg/kg doses of NAC were given to mice I.P. 2 h after collagenase infusion and thereafter in the mice efficacy studies. Saline was used as a control. The body temperature, edema, eicosanoids, cerebral bleeding, behavior, and lesion volume (28 day survival) of the animals were assessed. Animals were randomly assigned to groups, and data were analyzed blind.

Primary cortical neuronal cultures: Primary cortical neurons were collected from embryonic (E15) CD1 mice. The cortices of the mice were dissected, homogenized, and plated in minimum essential medium containing 10% fetal bovine serum (FBS), 5% horse serum, and 1% penicillin/streptomycin in 96-well plates, 6-well plates, or 10-cm dishes. The neurons were maintained at 37° C. with 5% $CO_2$. All experiments were conducted 24 hours after plating.

In vitro ICH model: Ferroptosis is a type of programmed cell death that is dependent on iron, and is characterized by the accumulation of lipid peroxides. Ferroptosis is genetically and biochemically distinct from other forms of regulated cell death such as apoptosis. Ferroptosis is initiated by the failure of the glutathione-dependent antioxidant defenses, resulting in unchecked lipid peroxidation and eventual cell death.

Cell death was induced in primary cortical neurons by treating the neurons with hemin, a blood breakdown product. For the neuroprotection studies, cells were treated with hemin (100 µM) in the presence of NAC (0.1 mM to 1mM), 6-hydroxy-2,5,7,8-tetramethylchroman-2-carboxylic acid (trolox; 0.1 µM to 100 µM), β-carotene (0.1 µM to 100 µM) α-lipoic acid (0.01 mM to 2 mM), glutathione ethyl ester (1 mM to 10 mM), oxothiazolidine-4-carboxylate (1 mM to 10 mM), cystamine (0.1 µM to 10 µM), or nordihydroguaiaretic acid (0.1 µM to 10 µM). Cell viability was analyzed 24 h after treatment. The cells were rinsed with warm phosphate-buffered saline (PBS) and assessed using an MTT assay. The fidelity of the MTT assays in measuring viability was verified by calcein-AM/ethidium homodimer-1 staining (Live/Dead assay).

In vivo collagenase-induced mouse model of ICH: Male C57BL/6 mice (8 to 10 weeks of age) or mice (10 to 12 weeks of age) were anesthetized with isoflurane (2% to 5%) and placed on a stereotaxic frame. During the procedure, the animal's body temperature was maintained at 37° C. with a homeothermic blanket. 1 mL of collagenase (0.075 IU) was infused into the right striatum at a flow rate of 0.120 µL/min using a Nanomite® syringe pump and a syringe. Relative to the bregma point, the stereotaxic coordinates of the injection were: lateral, −0.20; anteroposterior, 0.62; and dorsoventral, −0.40. In control animals, 1 mL of saline was infused. The treatment group received NAC (75 mg/kg or 300 mg/kg in normal saline, I.P.) once a day for 7 days starting at 2 h after collagenase infusion. For combinatorial studies, NAC (40 mg/kg, I.P.) and PGE 2 (10 µM, ICV) were administered to the mice 2 h after the collagenase injection, and then NAC (40 mg/kg) was administered once daily for 7 days. The control groups received the vehicle (normal saline) alone. The animals were randomized to sham or ICH groups. The identities of the mice that received vehicle or NAC were masked to surgeons who performed the experiments. The identities of the animals were revealed after collection of the data. Proper postoperative care was provided until the animals recovered completely.

Behavioral analysis: The corner task assessed integrated sensorimotor function in the stimulation of vibrissae (sensory neglect) and rearing (motor response). Mice were placed between two cardboard pieces that formed a corner with a 30° angle. While maintaining the 30° angle, the boards were gradually moved toward the mouse until the mouse approached the corner, reared upward, and turned 180° to face the open end. The direction (left or right) in which the mouse turned was recorded for each trial. Ten trials were performed for each mouse.

For the sensory neglect task (adhesive tape removal task), adhesive tape was placed on the planter region of the forward paw (right and left) of each mouse. The time from which the tape was applied to when the mouse successfully removed the tape was recorded for each paw. A maximum of 300 s for each paw was allowed.

Fluoro-Jade® B staining: Neurodegeneration of cells was assessed in mice with collagenase-induced ICH using Fluoro-Jade® B staining. 40 µM brain sections were mounted on gelatin-coated slides and dried at room temperature overnight. The sections were immersed in a graded series of alcohol solutions before being immersed in a 0.06% potassium permanganate ($KMnO_4$) solution for 15 min. Sections were washed with water before being immersed in a 0.001% Fluoro-Jade® staining solution with gentle shaking in the dark for 30 min. The sections were then washed with water and dried overnight at room temperature in the dark before being dehydrated and coverslipped with DPX. Fluoro-Jade® B staining was examined within perihematoma or hematoma regions using a fluorescence microscope. Quantification of Fluoro-Jade® B staining was performed using three brain sections (anterior to posterior of hematoma) using Metamorph analysis.

In vivo metal distribution imaging analysis by X-ray fluorescence: Seven days following collagenase-induced ICH, mice were euthanized and perfused with trace metal-free PBS. The brains were removed from the mice and flash frozen. Tissue samples were cut into 20 µm-thick sections and deposited onto 4 µm-thick Ultralene® films. The iron and zinc contents of the tissue samples were imaged using X-ray fluorescence microscopy (XFM). X-ray fluorescence spectra were collected using an X-ray excitation energy of 11 keV and a beam size of 9 µm (vertical)×17 µm (horizontal) in 15-µm steps, with an integration time of 7 sec/pixel. The intensity for each metal was quantified by integrating the area under the curve for the respective peak in the XRF spectrum (iron K$\alpha$=6405 eV and zinc K$\alpha$=8637 eV).

National Institute of Standards and Technology thin film standard reference materials 1832 and 1833 were used to calculate concentrations and to normalize for any differences between the multiple beam time runs required to collect the data. Molar concentrations were determined by dividing the µm/cm$^2$ values by the product of the volume of X-ray beam on the sample (area×thickness of the sample), the density of tissue (estimated to be 0.9 g/cm$^3$), and the molecular weight of the element.

Transcriptomic analysis: Weighted Gene Coexpression Network Analysis (WGCNA) was performed using R software. Correlation coefficients were constructed between expression levels of genes, and a connectivity measure (topological overlap, TO) was calculated for each gene by summing the connection strength of a gene with other genes. The genes were then clustered based on the TO values, and groups of co-expressed genes (modules) were identified. Each module was assigned a color. The first principal component (eigengene) of a module was extracted from the module and considered to be representative of the gene expression profiles in a module. The phenotypic trait of interest was then regressed on the eigengene to examine the presence of a statistically significant relationship between the module and the trait. For modules that showed a statistically significant relationship with a phenotypic trait of interest (presence of ICH), gene ontology and pathway analyses were examined using Enrichr. Corrected p-values were used. The independent list of coexpressed genes was obtained from COEXPRESdb, version 6.0.

Quantitative real-time PCR: Total RNA was prepared using a NucleoSpin® RNA II kit. Duplex real-time PCR reactions were performed with gene expression assays using 6-carboxyfluorescein-labeled probes for ALOX5 (Mm 01182747_m1) and ALOX5AP (Mm 01218551_m1). Expression levels were normalized to β-actin gene expression levels, which were determined with a VIC™-labeled probe. All experiments were performed using a real-time PCR system.

Lipoxygenase UV/Vis-based IC$_{50}$ assay: Inhibition potencies were determined by following the formation of conjugated diene products, 5-HpETE [ε=27000 M$^{-1}$ cm$^{-1}$ for AA turnover) at 234 nm using a UV/Vis spectrophotometer. All reaction mixtures were 2 mL in volume, and the reaction mixtures were constantly stirred using a magnetic stir bar at room temperature (23° C.). All reactions were carried out in a buffer containing 200 µM ATP and 10 µM AA. The AA concentration of a sample was verified by full turnover with soybean-1 lipoxygenase and quantifying the product concentration. Inhibitors were stored in DMSO at −20° C. Enzymatic reactions were initiated by adding approximately 100 nM-300 nM ammonium sulfate-precipitated wildtype enzyme. IC$_{50}$ values were obtained by determining the enzymatic rate at a minimum of five inhibitor concentrations, plotting the enzymatic rate against inhibitor concentration, and performing a hyperbolic saturation curve fit. Inhibitor concentrations were assayed in duplicate or triplicate.

Statistical analyses: Data are reported as means±SEM of multiple individual experiments each carried out in triplicate. A two-tailed t test was used to compare two groups. A one-way ANOVA with Bonferroni's multiple comparisons post hoc test was used if more than two groups were compared. A two-way ANOVA with Bonferroni's post hoc test was used to compare two independent variables.

Example 2: NAC Abrogated Hemin Toxicity In Vitro; NAC Reduced Neuronal Death and Improved Functional Recovery in an In Vivo Model of ICH The ability of NAC to protect cells was investigated in a hemin model of hemorrhagic stroke. The in vitro model of ICH involved the administration of hemin, a breakdown product of hemoglobin from lysed blood, to trigger cell death. Treatment of primary cortical neurons with 100 µM hemin induced widespread cell death through a ferroptotic mechanism, which was quantified with MTT and qualitatively observed using live/dead staining. Living cells were labeled with calcein-AM, and dead cells were labeled with ethidium homodimer. FIG. 1 shows representative live/dead images of primary cortical neurons 24 h after treatment with saline (Ctrl), NAC (1 mM), hemin (100 µM) and hemin (100 µM)+NAC (1 mM). Scale bars: 100 µm.

Figure 2:
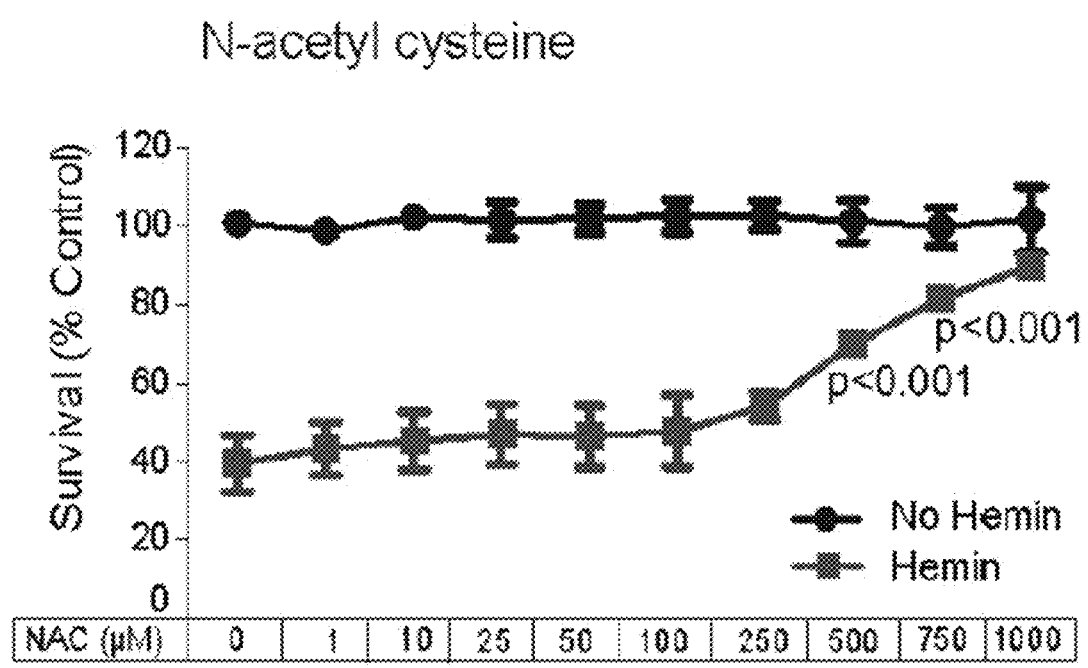
FIG. 2 shows that NAC protected primary cortical neurons from hemin-induced toxicity in a concentration dependent manner. The graph shows mean±SEM.

Treatment with NAC abrogated hemin-induced ferroptosis (EC$_{50}$=500 µM). To verify that NAC protected against hemin-induced toxicity in primary mouse neurons, primary cortical neurons were treated with various concentrations of NAC (100 nM-1 mM) alone or with hemin. Cell survival was assessed using MTT. FIG. 2 shows that NAC protected primary cortical neurons from hemin-induced toxicity in a concentration dependent manner. Cell death was analyzed 24 h after hemin treatment with or without NAC, and cell death was determined by monitoring MTT reduction. Significance was determined by two-way ANOVA and Bonferroni's post hoc test. The graph shows mean±SEM. The data show that NAC reduced cell death toxicity by hemin in primary neurons.

The ability of NAC treatment (300 mg/kg) to improve behavioral outcomes in an in vivo ICH model of hemorrhagic stroke was tested. The enzyme collagenase dissolves components of the extracellular matrix and basal lamina of blood vessels, leading to rupture of blood vessels and bleeding in the brain. Collagenase was injected into the mediolateral striatum of mice to break down the basal lamina and induce striatal brain bleeding. The collagenase model imitated the spontaneous rupture of an intra-parenchymal vessel with bleeding into the tissue over several hours.

Figure 3:
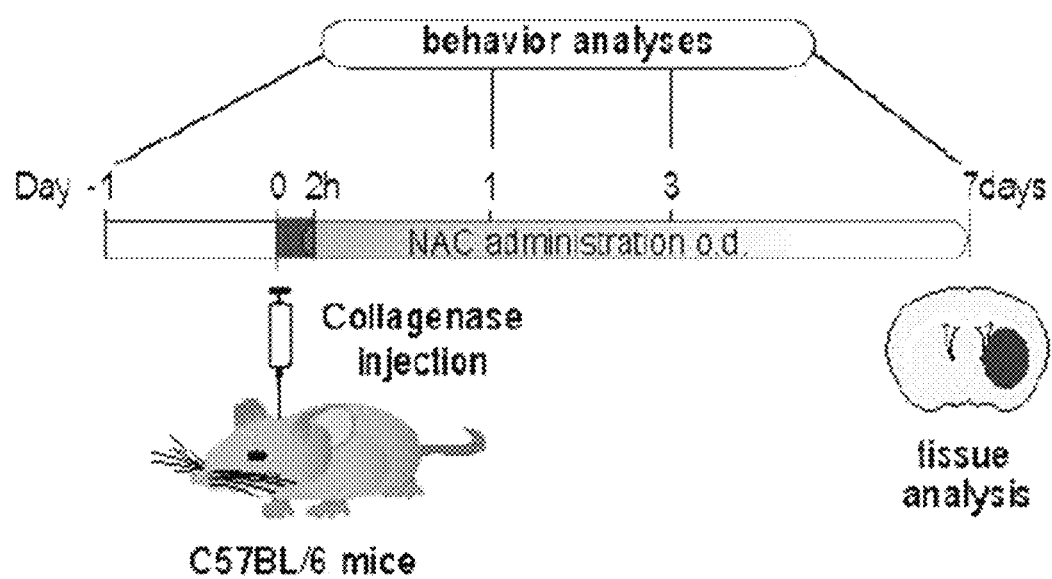
FIG. 3 shows a schematic of an experimental design for the delivery of NAC post-intracerebral hemorrhage (ICH) in mice.

Neuronal loss from sections of mice treated with vehicle or NAC (300 mg/kg, I.P.), and the ability of NAC to improve behavioral outcomes was evaluated by initially delivering the vehicle or NAC to mice starting 2 h after the unilateral injection of collagenase into the mouse striatum. The vehicle or NAC was then administered daily up to 7 days following the ictus. Neuronal loss was determined using a non-specific marker of neurodegeneration, Fluoro-Jade® staining. FIG. 3 shows a schematic of an experimental design for the delivery of NAC post-ICH in mice. Mouse behavior was assessed using a corner task (spatial neglect) and an adhesive tape removal task (sensory neglect). Mouse behavior was assessed on day 1, 3, and 7 after the induction of ICH.

Figure 4:
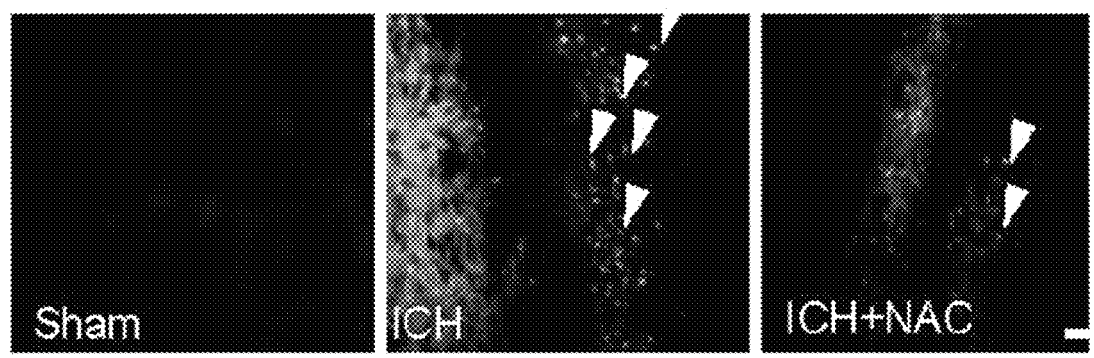
FIG. 4 shows that NAC reduced neuronal degeneration as monitored by Fluoro-Jade® staining in the perihematomal regions of the mouse brain. The white arrows highlight the increased numbers of degenerating neurons in the ICH-treated group (middle panel). Neuronal degeneration was reduced by treatment with NAC (right panel). Scale bar: 100 µm.
Figure 5:
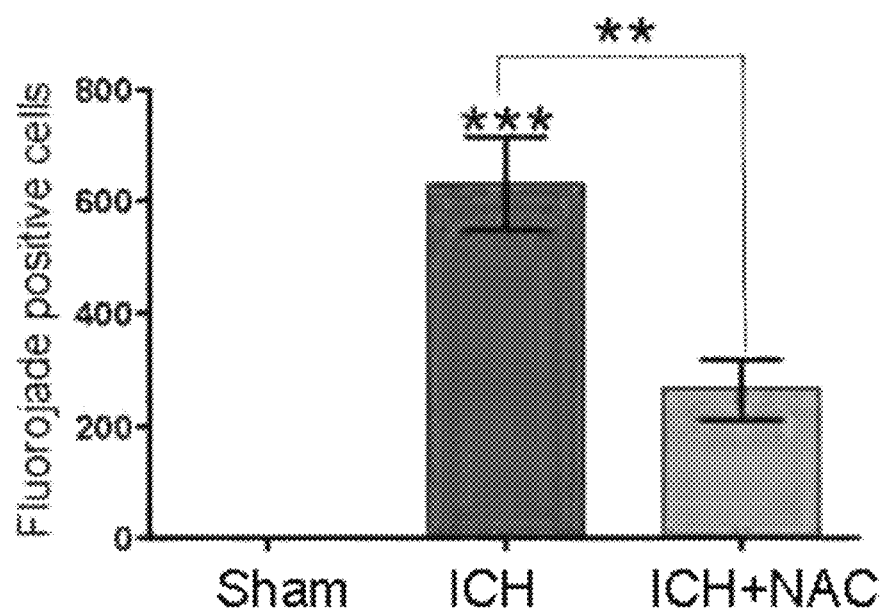
FIG. 5 shows the quantification of Fluoro-Jade® positive cells in sham-infused mice and in collagenase-infused ICH mice with or without NAC treatment. The graph shows mean±SEM.

The correlation of NAC-induced behavioral improvements with a reduction in ICH-induced neuronal degeneration was investigated. Mouse brain samples were assessed on day 7 using Fluoro-Jade® staining. NAC (300 mg/kg) reduced neuronal degeneration in perihematomal regions of the mouse brain. FIG. 4 shows that NAC reduced neuronal degeneration as monitored by Fluoro-Jade® staining in the perihematomal regions of the mouse brain. The white arrows highlight the increased numbers of degenerating neurons in the ICH-treated group (middle panel). Neuronal degeneration was reduced by treatment with NAC (right panel). Scale bar: 100 µm. FIG. 5 shows the quantification of Fluoro-Jade® staining of neurons, a non-specific marker of degeneration, in sham-infused mice and in collagenase-infused ICH mice with or without NAC treatment. Significance was determined by two-way ANOVA and Bonferroni's post hoc test. The graph shows mean±SEM. The data demonstrate that NAC reduced neuronal degeneration and improved sensorimotor deficits after ICH in a collagenase model.

Figure 6:
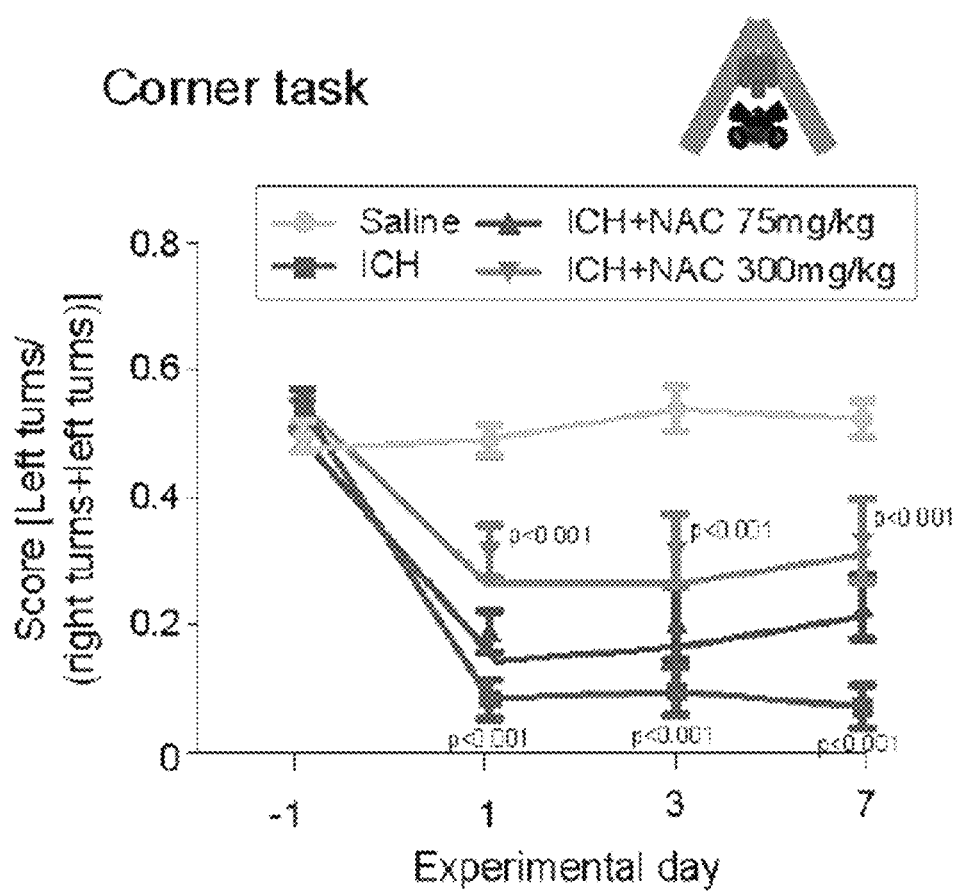
FIG. 6 shows the corner task scores on various experimental days for sham infused mice, collagenase infused ICH mice without NAC treatment, and collagenase infused ICH mice with NAC treatment at 75 mg/kg or 300 mg/kg. The graph shows mean±SEM.

The behavioral analysis, corner task (spatial neglect) and adhesive tape removal task (sensory neglect) were assessed on days 1, 3 and 7 after induction of ICH. Mice with striatal hemorrhage showed a preference for ipsilateral turns because of deficits in the weight-balancing movements of the limbs contralateral to the injury. Mice with striatal hemorrhage also exhibited spatial neglect. The preference for ipsilateral turns was normalized in NAC-treated mice, which was measured by the corner turn task. The deficits were corrected by administration of 300 mg/kg NAC, but not 75 mg/kg NAC, as measured by the corner turn task. FIG. 6 shows the corner task scores on various experimental days for sham infused mice, collagenase-infused ICH mice without NAC treatment, and collagenase-infused ICH mice with NAC treatment at 75 mg/kg or 300 mg/kg. The data show that administration of 300 mg/kg NAC significantly reduced spatial neglect associated with ICH. Significance was determined by two-way ANOVA and Bonferroni's post hoc test. The graph shows mean±SEM.

Figure 7:
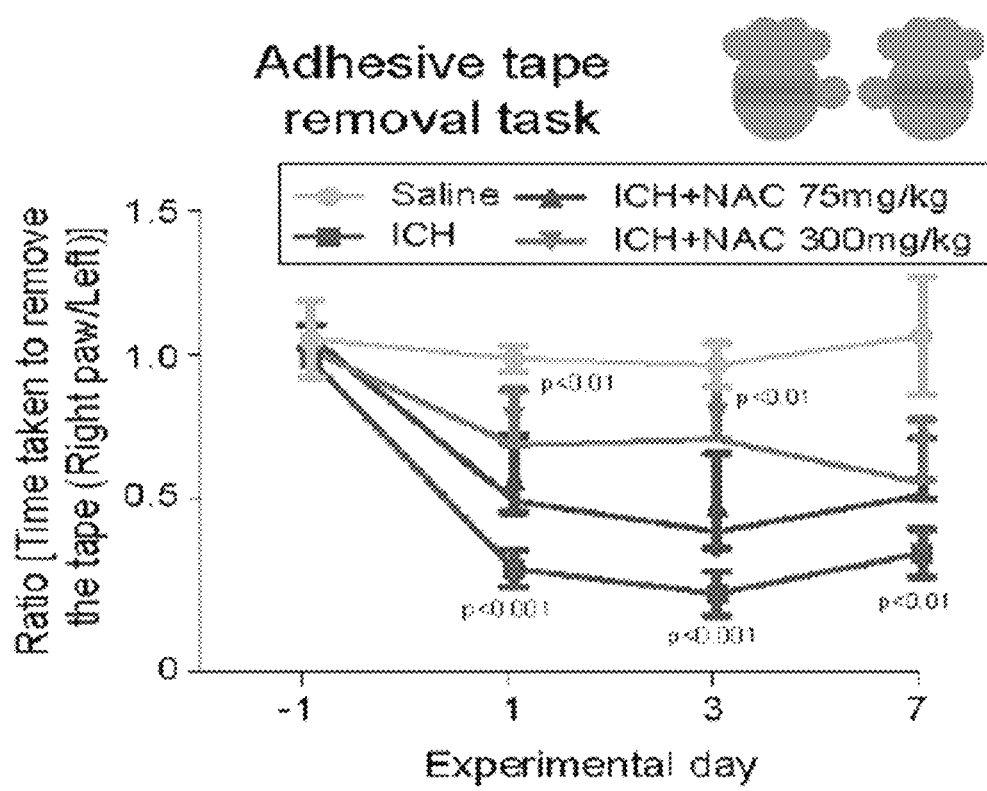
FIG. 7 shows showing the results of an adhesive tape removal task on various experimental days for sham-infused mice, collagenase-infused ICH mice without NAC treatment, or collagenase-infused ICH mice with NAC treatment at 75 mg/kg or 300 mg/kg. The graph shows mean±SEM.

The tape removal task is behavior that represents a form of sensory neglect. Analysis of the tape removal task showed that sensory neglect of NAC-treated mice 1, 3, and 7 days after ICH improved significantly. The improvements in sensory neglect were observed for mice treated with 300 mg/kg NAC, but not for mice treated with 75 mg/kg NAC. FIG. 7 shows the results of an adhesive tape removal task on various experimental days for sham-infused mice, collagenase-infused ICH mice without NAC treatment, or collagenase-infused ICH mice with NAC treatment at 75 mg/kg or 300 mg/kg. Significance was determined by two-way ANOVA and Bonferroni's post hoc test. The graph shows mean±SEM. The data show that NAC enhances functional recovery in the collagenase ICH mouse model.

The data shows that NAC (300 mg/kg) reduced cell death in vitro and in vivo, and improved behavior after ICH in mice. Examination of NAC in an ICH model of rats showed that 40 mg/kg was the highest dose tolerated without toxicity. Higher doses that were effective in mice (300 mg/kg) caused significant toxicity in rats, including paralytic ileus and/or death. NAC delivered at 40 mg/kg or 75 mg/kg in rats 2 h post-ICH was not effective in reducing lesion volume or improving functional recovery.

Example 3: NAC did not Influence Collagenase Enzyme Activity and Bulk Iron Chelation The collagenase-infused mouse model of ICH was used to study the mechanism of NAC protection in vivo. The mechanism of NAC protection in hemorrhagic stroke was investigated by verifying that the protective effects of NAC did not result from NAC's influence on collagenase enzyme activity, which was used to induce brain hemorrhage. The collagenase model for human brain ICH used collagenase to degrade the basal lamina of mice, generating hemorrhage that evolved in a way similar to that found in humans. The efficacy of NAC as a therapeutic to prevent death and enhance functional recovery was studied.

Figure 8:
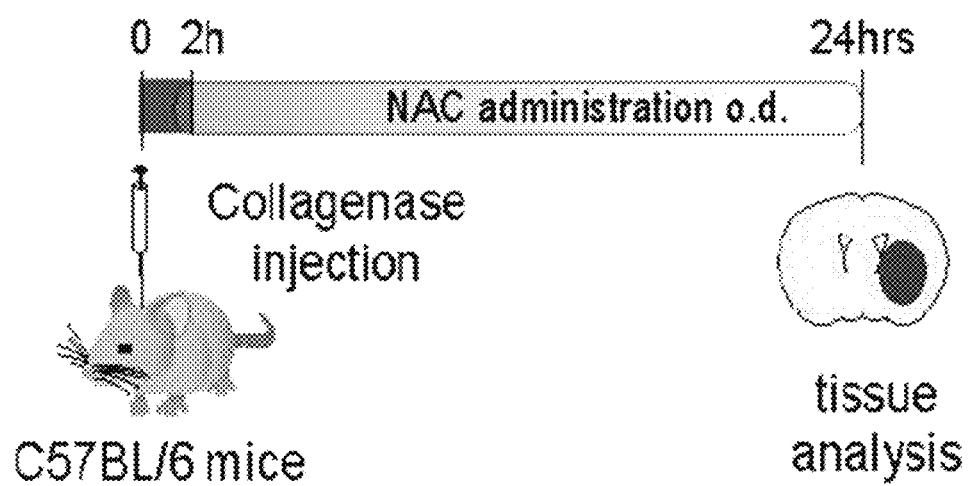
FIG. 8 shows a schematic of an experimental design investigating the effect of NAC in a collagenase-infused mouse model of ICH

Mice were injected with NAC 2 h post-ICH induction, and the mice were sacrificed after 24 h. The hematoma volumes of the mice were assessed. FIG. 8 shows a schematic of an experimental design investigating the effect of NAC in a collagenase-infused mouse model of ICH. Measurements of hematoma size 24 h after collagenase injection verified that NAC (300 mg/kg) did not inhibit or affect collagenase activity. The data demonstrate that the significant behavioral benefits could not be attributed to the suppression of collagenase activity by NAC.

Figure 9:
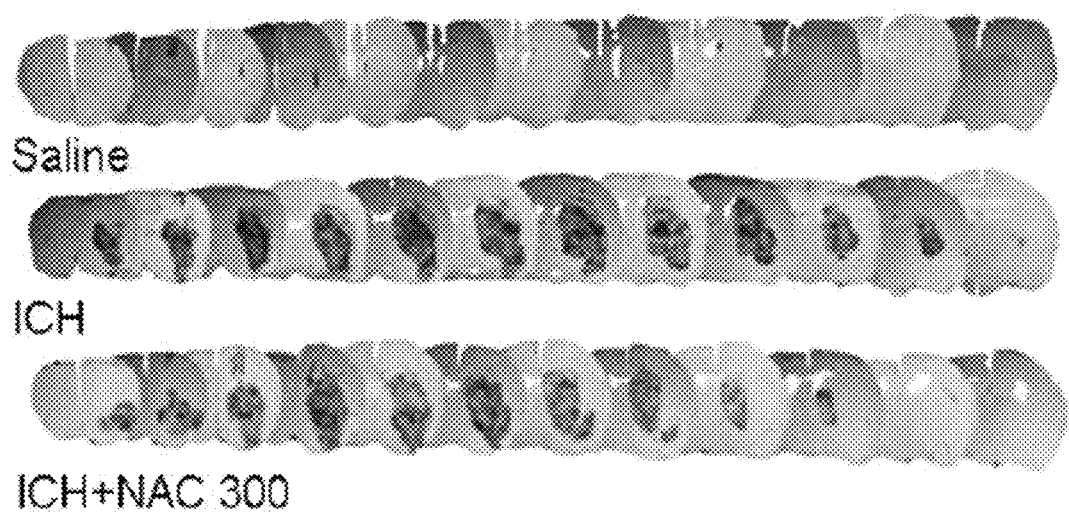
FIG. 9 shows a panel of serial brain sections from saline-treated mice and ICH mice with or without NAC treatment.
Figure 10:
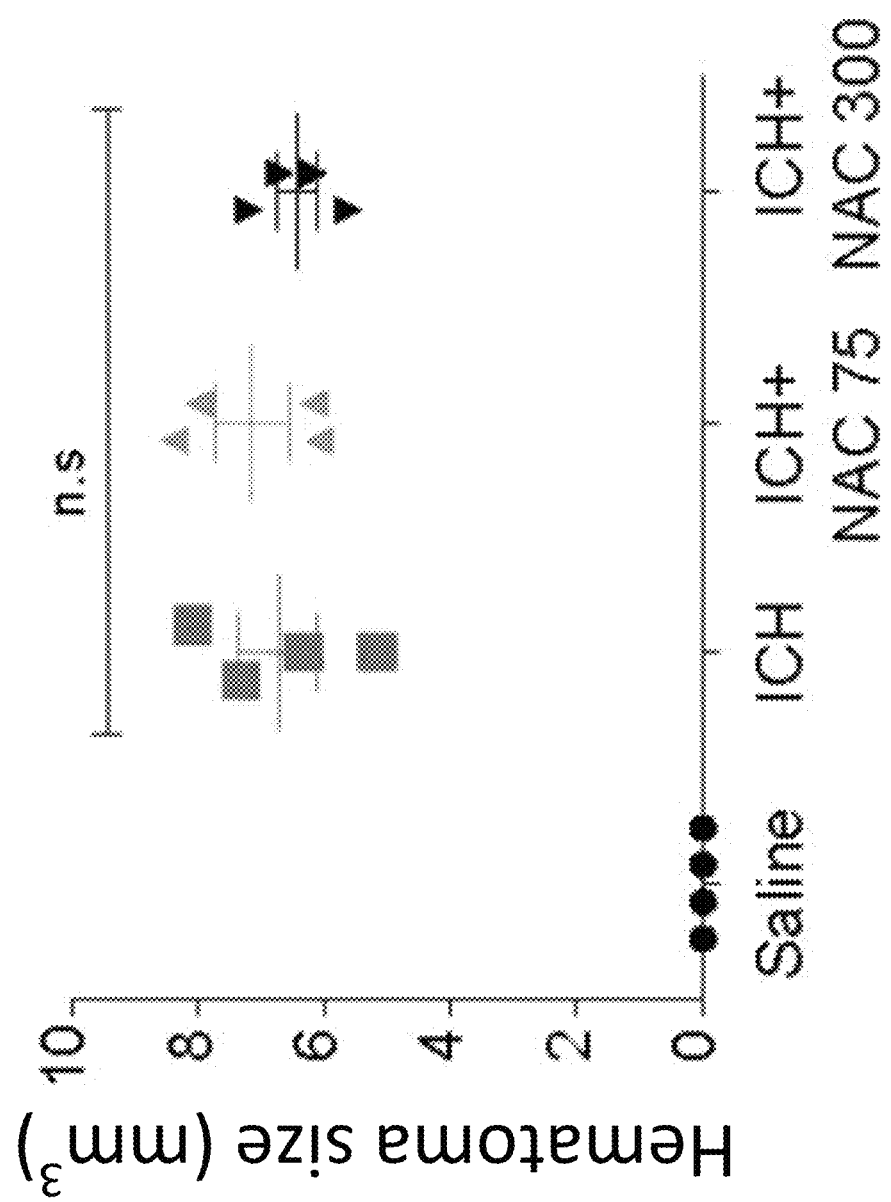
FIG. 10 shows a graph quantifying hematoma sizes by light microscopy in saline-infused mice, in untreated collagenase-infused ICH mice, and in collagenase-infused ICH mice treated with 75 mg/kg or 300 mg/kg of NAC. The graph shows mean±SEM.
Figure 11:
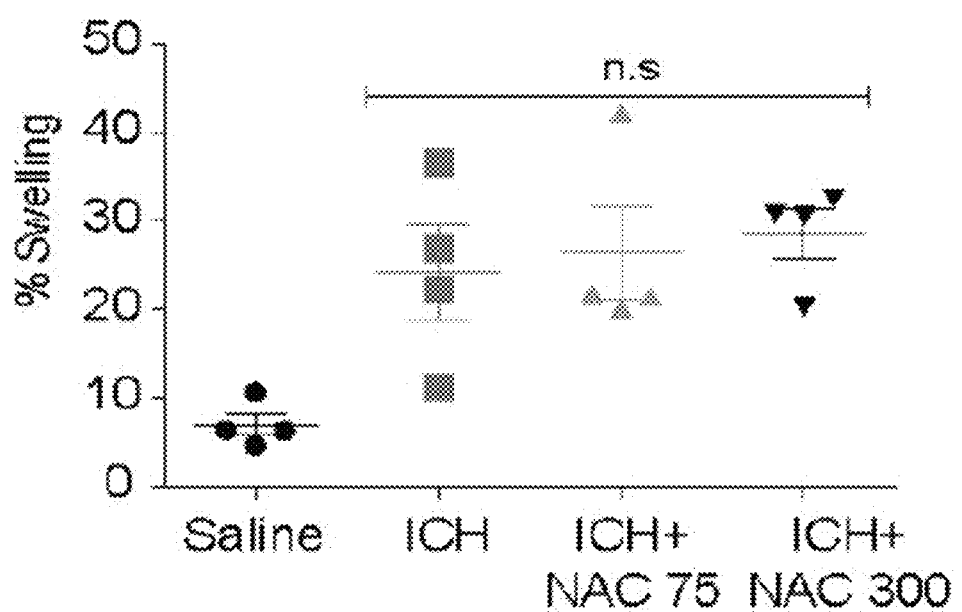
FIG. 11 shows a graph showing percentage of swelling (brain edema) by light microscopy in saline-infused mice, in untreated collagenase-infused ICH mice, and in collagenase-infused ICH mice treated with 75 mg/kg or 300 mg/kg of NAC. The graph shows mean±SEM.

FIG. 9 shows a panel of serial brain sections from saline-treated mice and ICH mice with or without NAC treatment. FIG. 10 shows a graph quantifying hematoma size by light microscopy in saline-infused mice, in untreated collagenase-infused ICH mice, and in collagenase-infused ICH mice treated with 75 mg/kg or 300 mg/kg of NAC. No significant difference was observed between the control group and the NAC treated groups. Significance was determined by one-way ANOVA followed by Dunnett's comparison test, for vehicle-treated mice and ICH mice with or without NAC treatment. The graph shows mean±SEM. FIG. 11 shows a graph showing percentage of swelling (brain edema) by light microscopy in saline-infused mice, in untreated collagenase-infused ICH mice, and in collagenase-infused ICH mice treated with 75 mg/kg or 300 mg/kg of NAC. Significance was determined by one-way ANOVA followed by Dunnett's comparison test, for vehicle-treated mice and ICH mice with or without NAC treatment. The graph shows mean±SEM.

Figure 12:
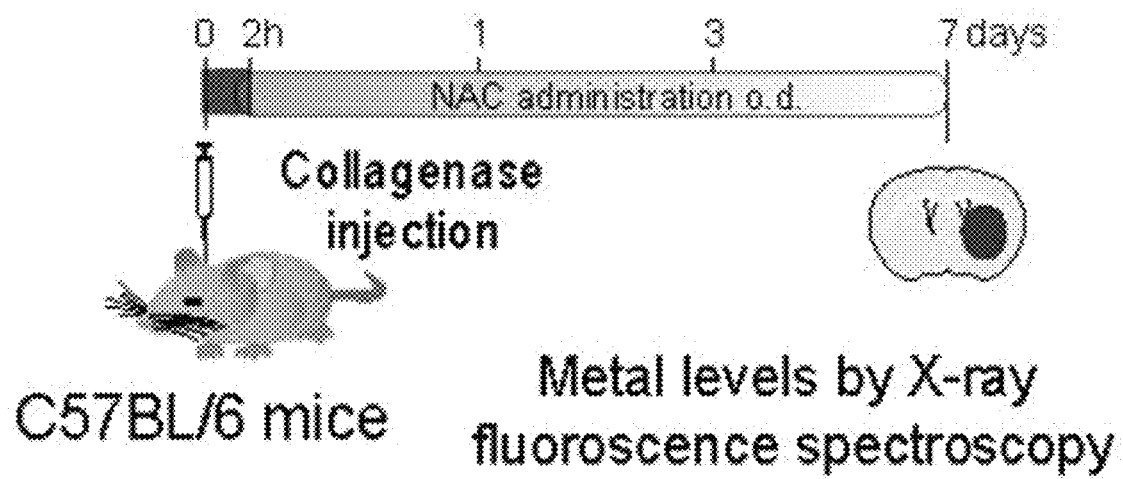
FIG. 12 shows a schematic of an experimental design for evaluating the total concentrations of iron in the brain following ICH in vehicle-treated and NAC-treated mice.

The ability of NAC to affect total metal levels in the brain was evaluated. Total iron levels in brain sections from saline-treated and NAC-treated ICH mice were monitored at 7 days using X-ray fluorescence spectroscopy. FIG. 12 shows a schematic of an experimental design for evaluating the total concentrations of iron in the brain following ICH in vehicle-treated and NAC-treated mice. Pseudo coloring in the coronal sections of collagenase-induced ICH mice after 7 days denotes total iron.

Figure 13:
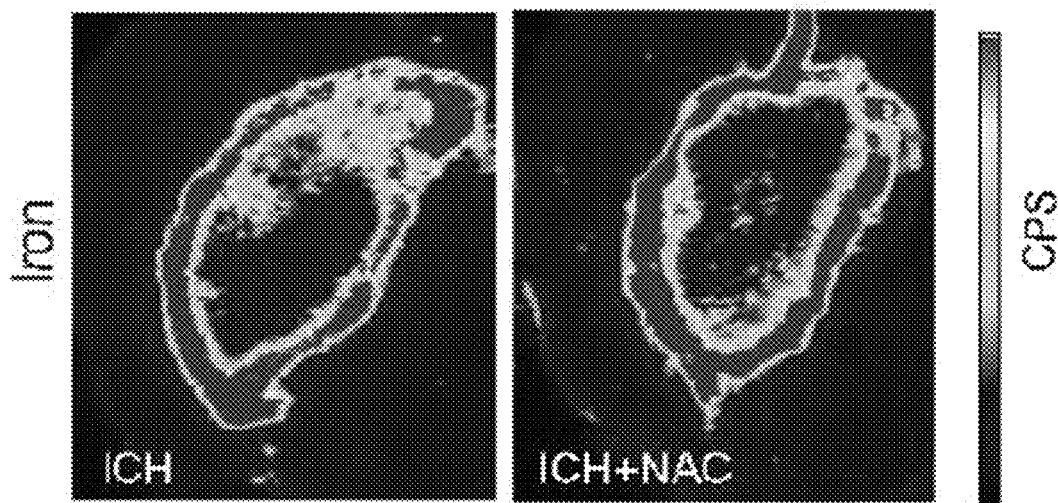
FIG. 13 PANEL A shows X-ray fluorescence spectroscopy images from coronal sections in collagenase-infused ICH mice with or without NAC treatment after 7 days.
Figure 13:
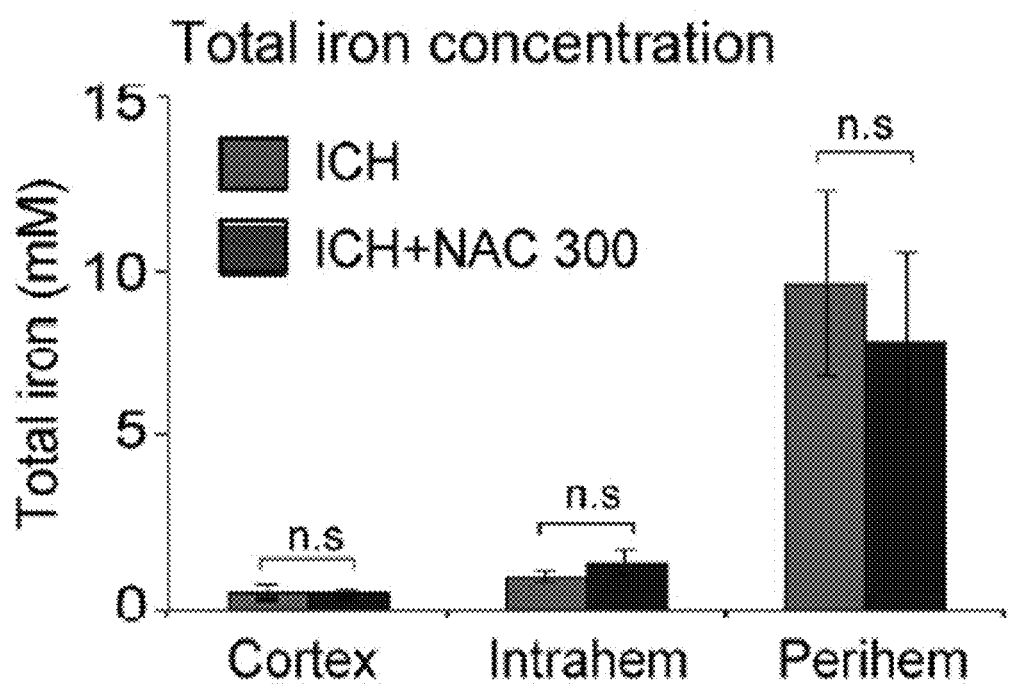

ICH dramatically increased iron levels in the brain. No difference was observed in the apparent distribution or total levels of iron between the brain sections of saline-treated and NAC-treated ICH mice. NAC had no effect on iron levels or iron distribution following ICH. The data show that NAC acted to protect ICH independently from NAC's effects on total iron levels or iron distribution in the CNS. FIG. 13 PANEL A shows X-ray fluorescence spectroscopy images from coronal sections in collagenase-infused ICH mice with or without NAC treatment after 7 days. FIG. 13 PANEL B shows total iron levels in the cortex, intrahematomal, and perihematomal regions of the brain of collagenase-infused ICH mice with or without NAC treatment. Significance was determined by one-way ANOVA followed by Dunnett's comparison test, for vehicle-treated mice and ICH mice with or without NAC treatment. The graph shows mean±SEM. The data show that NAC enhanced functional recovery without influencing collagenase activity in vivo or total levels of iron in the brain after ICH.

Example 4: NAC Failed to Synergize with Other Antioxidants

Figure 14:
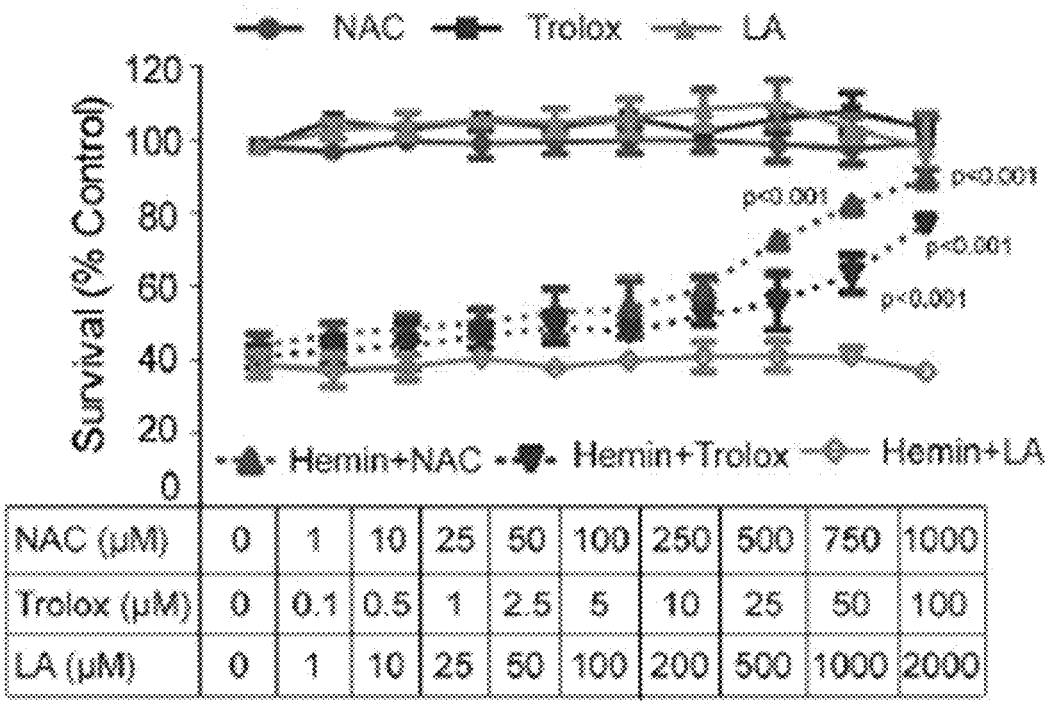
FIG. 14 PANEL A shows the effect of NAC, trolox (TRO), and α-lipoic acid (LA) in preventing hemin-induced ferroptosis in primary cortical neurons as measured by MTT assay.
Figure 14:
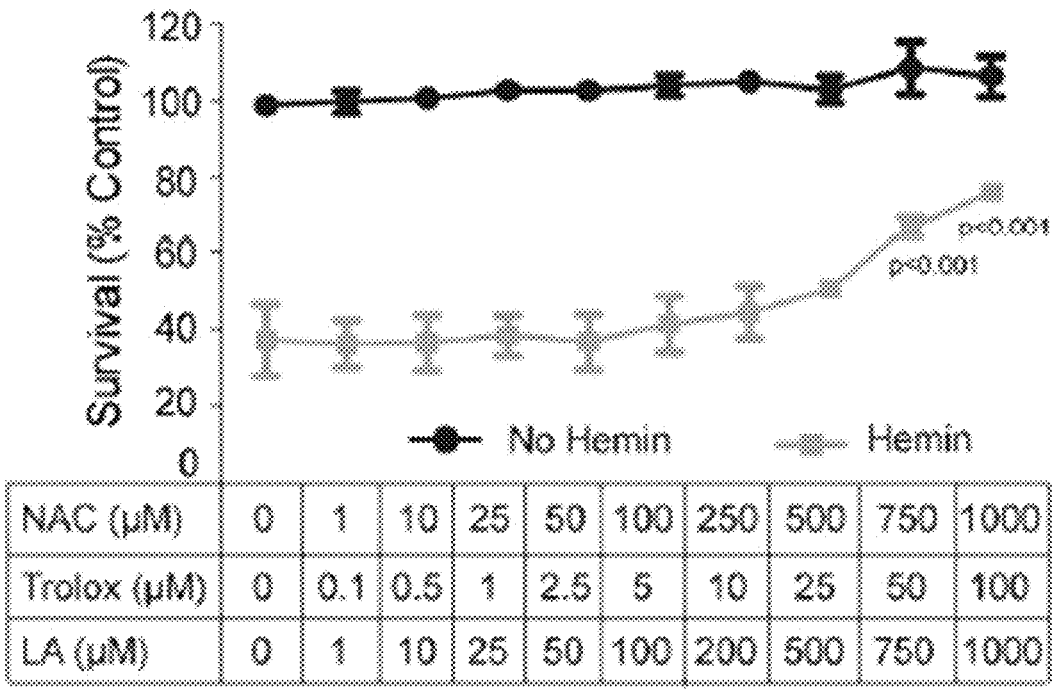

The ability of NAC to synergize with antioxidants was evaluated. A lack of synergy would suggest target congruence between the antioxidant with a known target of action and NAC. Trolox is a water soluble analogue of vitamin E and a scavenger of lipid peroxyl radicals. α-Lipoic acid is a thiol-active compound that acts as a cofactor for mitochondrial enzymes, reducing mitochondrial superoxide production. The effects of NAC, trolox, and α-lipoic acid individually and in combination were studied in mouse cortical neurons exposed to hemin. Treatment of NAC or trolox individually abrogated hemin-induced toxicity in a dose-dependent manner. α-Lipoic acid failed to prevent hemin toxicity at any dose examined. FIG. 14 PANEL A shows the effect of NAC, trolox (TRO), and α-lipoic acid (LA) in preventing hemin-induced ferroptosis in primary cortical neurons as measured by MTT assay.

To determine the synergistic effects of NAC with trolox and α-lipoic acid, sub-threshold concentrations of NAC and the compounds were administered together in a hemin model. All combinations of the cocktail of antioxidants failed to provide any synergistic protection against hemin toxicity in primary cortical neurons, which was consistent with a convergent mechanism at the level of lipid peroxidation. FIG. 14 PANEL B shows that combinations of non-protective concentrations of NAC, TRO, or LA failed to synergize in preventing hemin-induced ferroptosis in primary cortical neurons.

Example 5: NAC Prevented Hemin-Induced Death by Neutralizing Toxic Lipids Generated Via Nuclear ALOX5

Reactive lipid oxidants can be produced enzymatically via specific enzymes, or non-enzymatically via direct oxidant modification. Structurally diverse, but well characterized pharmacological tools were used to understand how hemin kills neurons. Neuronal membranes are composed of phospholipid bilayers where arachidonic acid (AA) is esterified into phosphatidylcholine, phosphatidylserine, and phosphatidylinositol. Following brain injury, AA is liberated by increases in calcium-dependent, phospholipase A2, or phospholipase C activity. Released AA can be oxidized non-enzymatically by oxidants or enzymatically by cyclooxygenase, lipoxygenase, or epoxygenase enzymes to produce bioactive lipid mediators, such as isoprostanes, hydroxynonenol, malondialdehyde, hydroxy-PUFAs (HETEs), epoxy-PUFAs (EETs), prostaglandins, and leukotrienes, which regulate homeostatic and inflammatory processes.

A systematic pharmacological screening of oxidized lipid species inhibitors in the context of hemin-induced cell death was performed in primary cortical neurons. Primary cortical neurons were co-treated with hemin and a non-specific or enzymatic lipid peroxidation inhibitor. The MTT assays were performed 18 h following the co-treatment. The screening identified the non-specific inhibitor β-carotene and selective 5-lipoxigenase (5-LOX) inhibitors as agents that protected against hemin-induced toxicity in primary cortical neurons.

A systematic characterization of AA-metabolizing enzymes involved in hemin-induced toxicity was conducted using a cassette of known, diverse chemical inhibitors. Selective inhibitors of epoxygenases (MS-PPOH), COX-1 (aspirin), COX-2 (celecoxib, Indomethacin), 12-LOX (NCTT-956), or 15-LOX (PD146176) failed to protect against hemin toxicity. Structurally diverse ALOX5 inhibitors (Zileuton, $EC_{50}=7$ μM; BW B70, $EC_{50}=$μM and BW 4AC, $EC_{50}=5$ μM) significantly reduced hemin-induced toxicity in primary cortical neurons.

NAC protection in an in vitro model of ICH was mimicked by structurally diverse inhibitors of ALOX5. TABLE 1 shows that structurally diverse inhibitors of 5-lipoxygenase, but not inhibitors of other arachidonate metabolizing enzymes, prevented hemin-induced ferroptosis in primary cortical neurons.

TABLE 1

| In vitro model of hemorrhagic stroke | | | | % Viability |
|---|---|---|---|---|
| Hemin-induced toxicity in neurons | | Vehicle | | 100.00 |
| | | 100 μM hemin | | 50.14 |
| Lipid peroxidation | Subcategory | Pharmacological inhibitor | Target | % viability |
| Phospholipids | Phospholipases | U 73122 Non-specific | Phospholipase C and A2 | 47.37 |
| Nonesterified arachidonic acid | Antioxidants | β-carotene | Oxidants | 88.12 |
| | | Enzymatic | | |
| Epoxygenases | Epox | MS-PPOH | Epoxygenases | 61.3 |
| Cyclooxygenases | COX1 | Aspirin | Cycloxygenases 1 | 50.20 |
| | COX2 | Celecoxib | Cycloxygenases 2 | 45.3 |
| | | Indomethacin | Cycloxygenases 2 | 54.9 |
| Lipoxygenases | 5 LOX | Zileuton | 5 lipoxygenases | 93.70 |
| | | BW B70 | 5 lipoxygenases | 90.20 |
| | | BW A4C | 5 lipoxygenases | 86.70 |
| | 12 LOX | NCTT-956 | 12 lipoxygenases | 63.5 |
| | 15 LOX | PD146176 | 15 lipoxygenases | 59.3 |
| | FLAP | MK 561 | 5 lipoxygenase-activating protein | |

Figure 15:
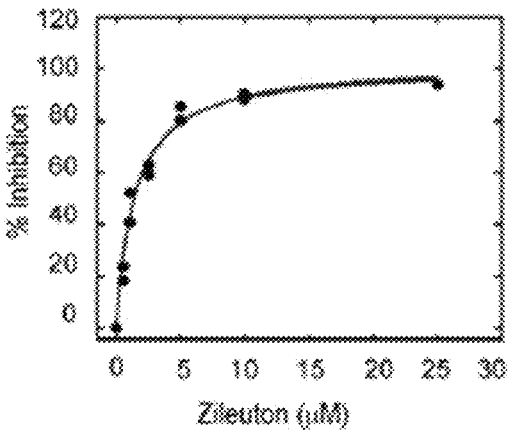
FIG. 15 PANEL A shows that Zileuton was effective in inhibiting ALOX5.
Figure 15:
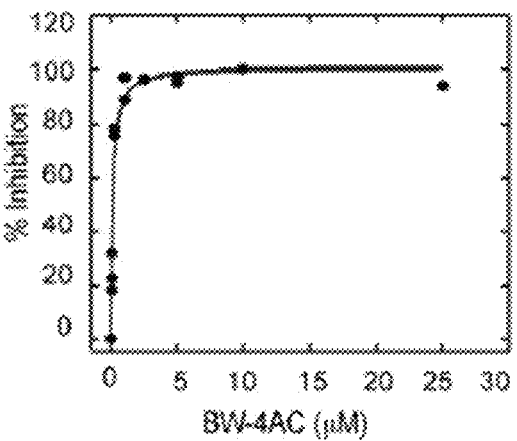
Figure 15:
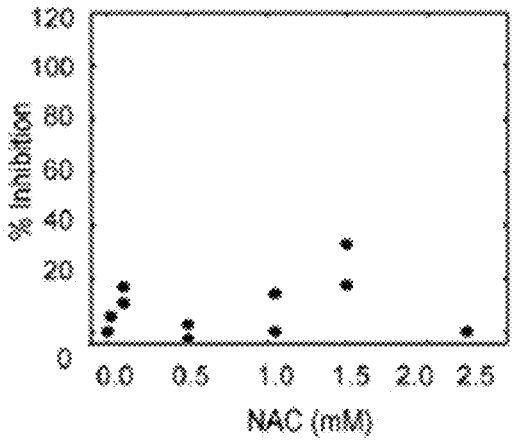

Test tube assays involving recombinant ALOX5 verified that each of the inhibitors inhibited ALOX5 activity with high potency. NAC and β-carotene, which were protective, did not inhibit ALOX5 activity. FIG. 15 PANEL A shows that Zileuton was effective in inhibiting ALOX5. FIG. 15 PANEL B shows that BW-4AC was effective in inhibiting ALOX5. FIG. 15 PANEL C shows that NAC was not effective at inhibiting ALOX5. Significance was determined by two-way ANOVA and Bonferroni's post hoc test.

The data show that 5-lipoxygenase-derived lipid metabolites are necessary for hemin-induced ferroptosis in vitro. The data also show NAC, trolox, and β-carotene may act to neutralize the toxic metabolic products of ALOX5 activity rather than ALOX5 activity itself. Inhibitors of arachidonate-5-lipoxygenase activating protein (FLAP), an integral membrane protein within the nuclear envelope, which serves to recruit ALOX5 to the membrane, may also be protective. TABLE 1 shows that a chemical FLAP inhibitor (MK 561) significantly reduced hemin-induced death.

Figure 16:
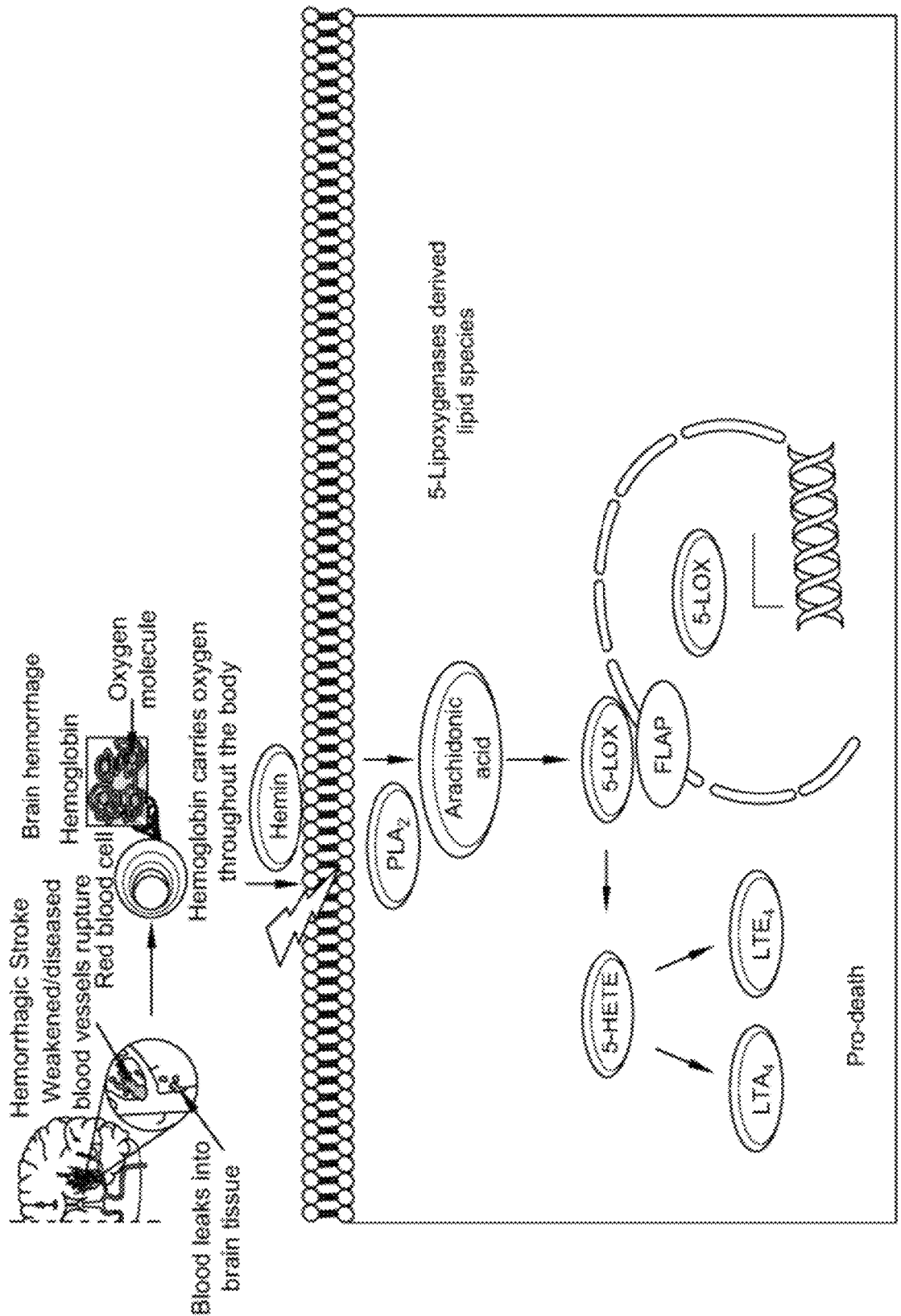
FIG. 16 illustrates a schematic model of ALOX5 pathway activation in ICH.

Example 6: ICH Induced Nuclear ALOX5 Protein In Vitro and ALOX5-Derived Gene Expression In Vivo The pharmacological data demonstrated that ALOX5 mediated cell death in vitro by localizing to the nuclear envelope via interactions with FLAP. The ability of ICH to induce ALOX5 levels in the cytoplasm or nucleus was determined. Increases in ALOX5-derived AA species following ICH were assayed. FIG. 16 illustrates a schematic model of ALOX5 pathway activation in ICH.

Figure 17:
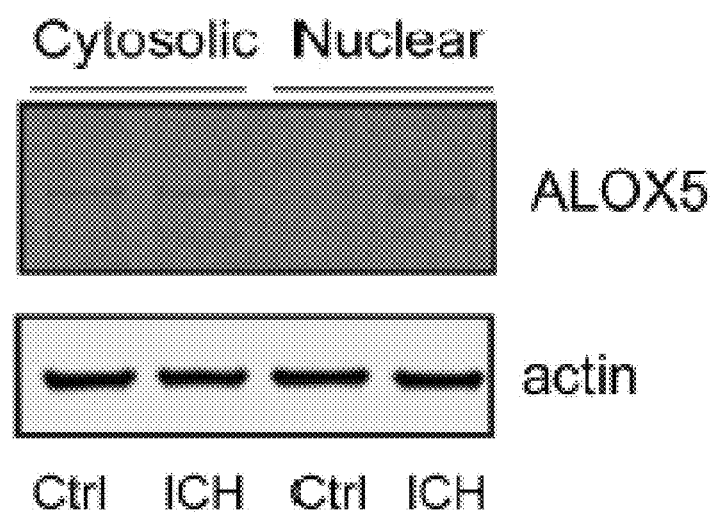
FIG. 17 shows that ICH increased ALOX5 protein levels in nuclear fractions, as verified by immunoblot analysis.

Protein levels of ALOX5 in the nucleus after ICH were analyzed. Immunoblot analysis of the cytosolic and nuclear fraction after ICH revealed that ALOX5 increased in the nucleus. FIG. 17 shows that ICH increased ALOX5 protein levels in nuclear fractions, as verified by immunoblot analysis.

Figure 18:
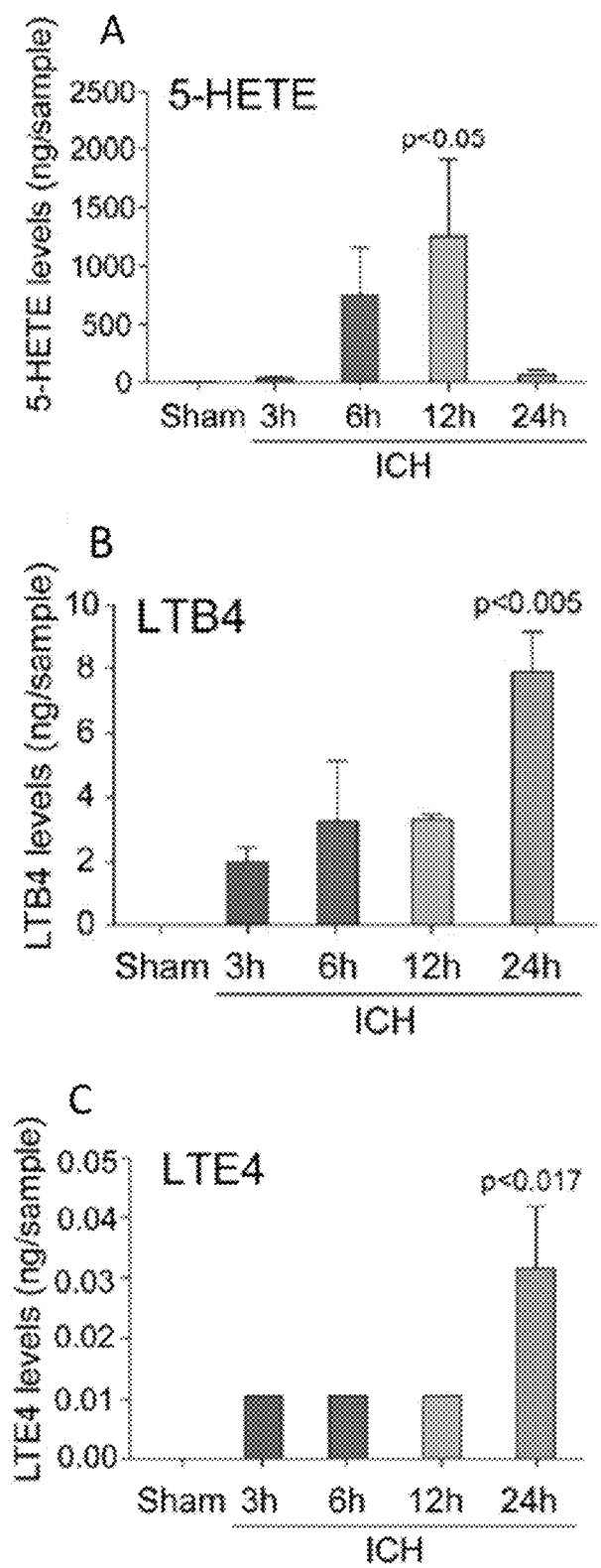
FIG. 18 PANEL A shows the increase in ALOX-derived 5-HETE after induction of ICH in rats.

ALOX5 metabolizes AA to produce 5-hydroperoxyeicosatetraenoic acid (5-HPETE), which forms the inflammatory mediators leukotriene B4 (LTB4) and cysteinyl leukotrienes (CysLTs, including LTC4, LTD4, and LTE4). The metabolites of ALOX5 were monitored using gas chromatography/negative ion chemical ionization mass spectrometry (GC/MS) to assess the activation of ALOX5 in a rodent model of ICH. GC/MS analysis of ICH striatum showed a significant time-dependent increase in the ALOX5 products: 5-HETE, LTB4, and LTE4. The increase in ALOX5-derived lipid species after ICH in rats (n=4) was compared to sham. Data from sham control brains from each time point was pooled for the analysis. FIG. 18 PANEL A shows the increase in ALOX-derived 5-HETE after ICH in rats. FIG. 18 PANEL B shows the increase in ALOX-derived LTB4 after induction of ICH in rats. FIG. 18 PANEL C shows the increase in ALOX-derived LTE4 after induction of ICH in rats. The data were consistent with transcriptomic analyses of brain tissues from human ICH patients that identified an increased expression of mRNAs encoding ALOX5 and 5-LOX-activating protein FLAP (ALOX5AP). The increases in ALOX5 metabolites after ICH in mice and rats showed that toxic factors downstream of hemorrhage also produced reactive lipid species in vivo.

Figure 19:
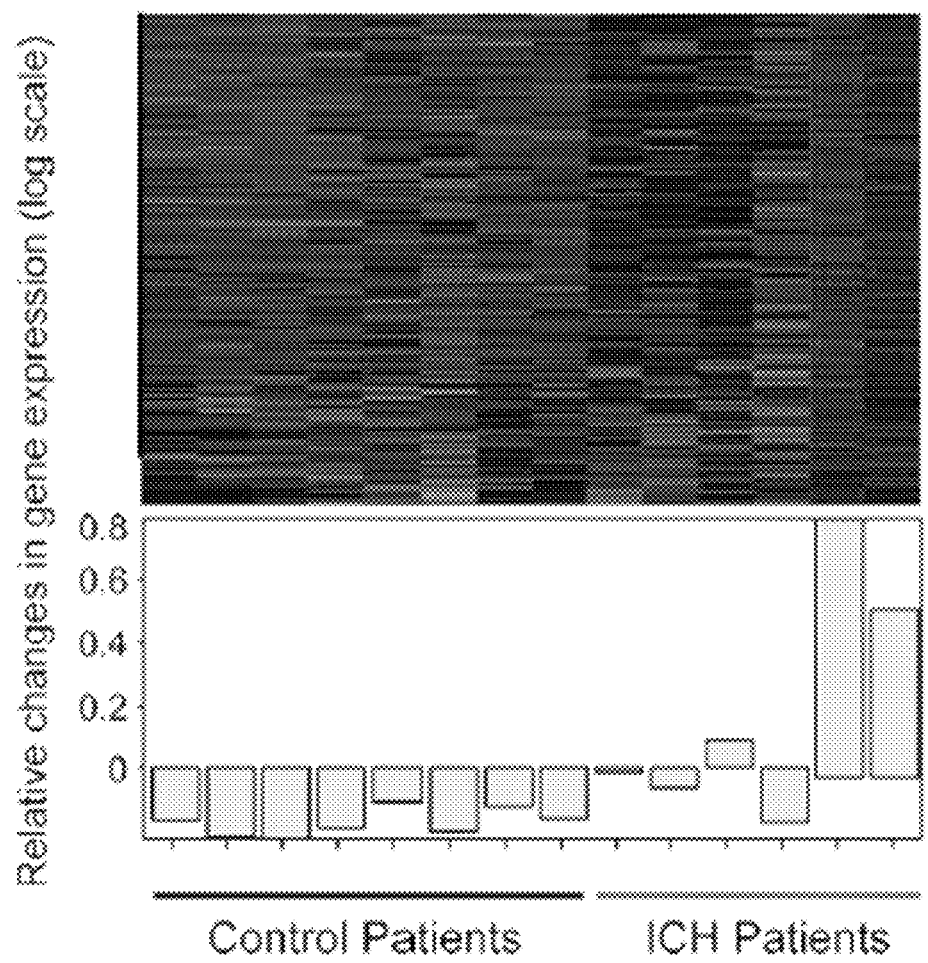
FIG. 19 shows the results of the transcriptomic analysis of brain tissues obtained from control (n=8) and ICH (n=6) patients.

To explore the network of transcripts co-expressed with ALOX5, human gene expression data were analyzed using 8 control samples and 6 samples obtained from patients with ICH. Weighted Gene Coexpression Network Analysis (WGCNA) was used to identify networks of co-expressed genes in relation to phenotypic data. WGCNA identified 21 groups of co-expressed genes/modules. ALOX5 was included in the greenyellow module, a group of 302 transcripts overall upregulated in ICH. FIG. 19 shows the results of the transcriptomic analysis of brain tissues obtained from control (n=8) and ICH (n=6) patients. Significance was determined by one-way ANOVA and Dunnet's multiple comparison test. All graphs are mean±SEM.

Figure 20:
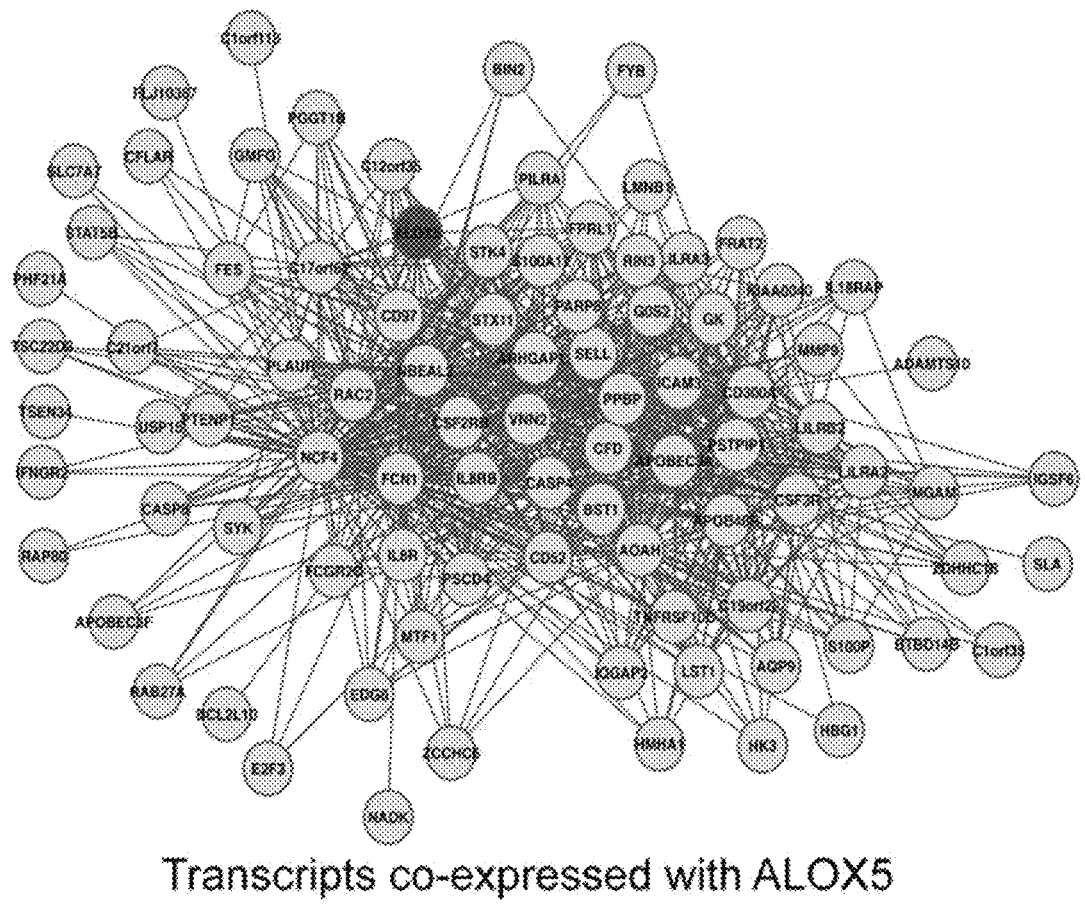
FIG. 20 shows that WGCNA revealed transcripts most closely co-regulated with ALOX5.

The top 100 transcripts correlated with ALOX5 were extracted from a large transcriptional database (COEXPRESdb). Functional annotation of the module revealed over-representation of genes involved in inflammation in general and neutrophil degranulation. Functional annotation of the transcripts revealed similar ontology terms. Fifteen of the 100 transcripts were included in the WGCNA greenyellow module, and a significant overlap (p=8×10E-9, hypergeometric test) provided independent validation of the WGCNA analysis. The findings demonstrated that ICH induced accumulation of ALOX5 in the nucleus to increase ALOX5-derived lipid species, which triggered cell death and/or represented a signal sent from the nuclear envelope of dead cells to trigger inflammation. FIG. 20 shows that WGCNA revealed transcripts most closely co-regulated with ALOX5.

Example 7: NAC Reduced ICH-Induced ALOX5 Gene Expression and Reactive Lipids

Figure 21:
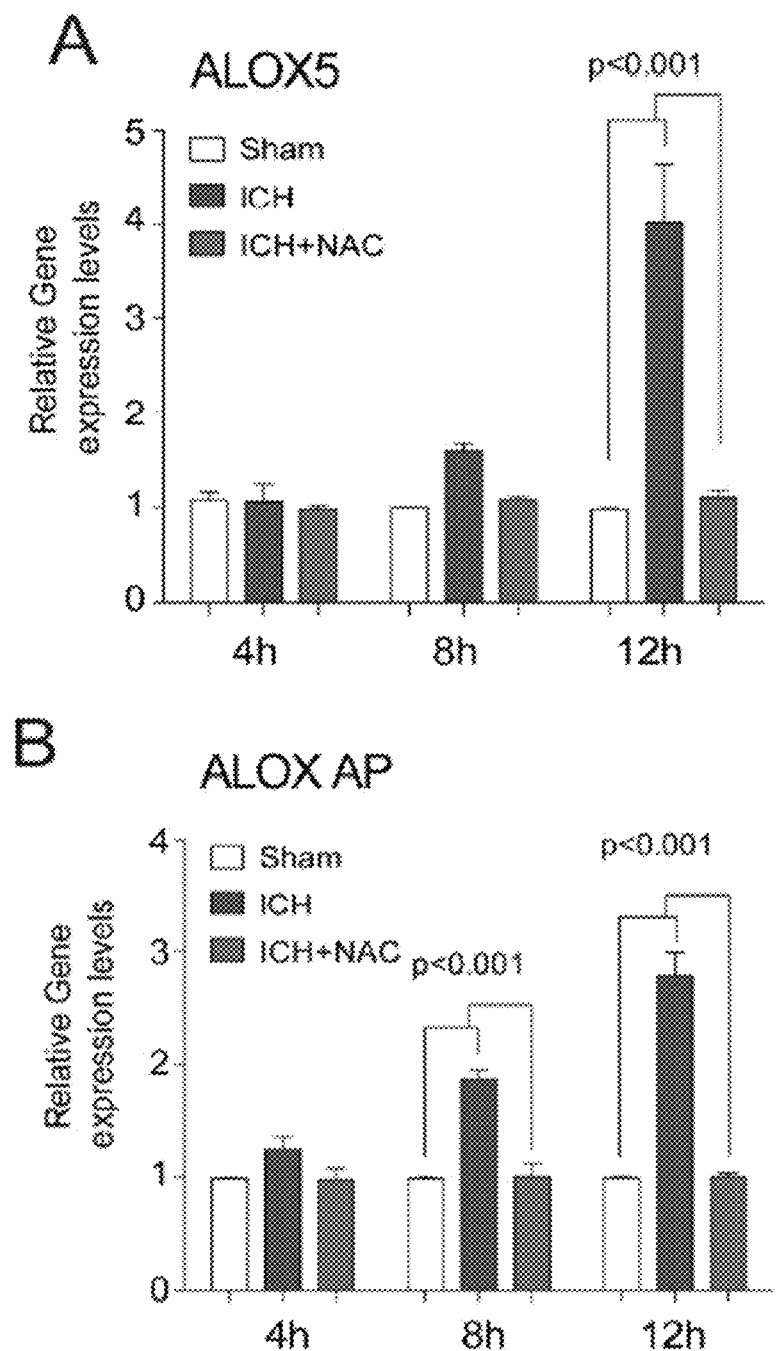
FIG. 21 PANEL A shows that hemin increased ALOX5 levels in a time-dependent manner, while NAC blocked the expression of ALOX5 in primary cortical neurons.

The abilities of hemin and NAC to induce increases in ALOX5 and ALOX AP mRNA levels were examined. RT-PCR analysis revealed that toxic levels of hemin increased ALOX5 and ALOX AP levels in primary neurons. Consistent with the protein data (FIG. 17), hemin induced increases in ALOX AP and ALOX5 mRNA levels in a time-dependent manner. Protective doses of NAC (1 mM) blocked the expression of ALOX5 and ALOX AP in primary cortical neurons. FIG. 21 PANEL A shows that hemin increased ALOX5 levels in a time-dependent manner, while NAC blocked the expression of ALOX5 in primary cortical neurons. FIG. 21 PANEL B shows that hemin increased ALOX AP levels in a time-dependent manner, while NAC blocked the expression of ALOX AP in primary cortical neurons.

Figure 22:
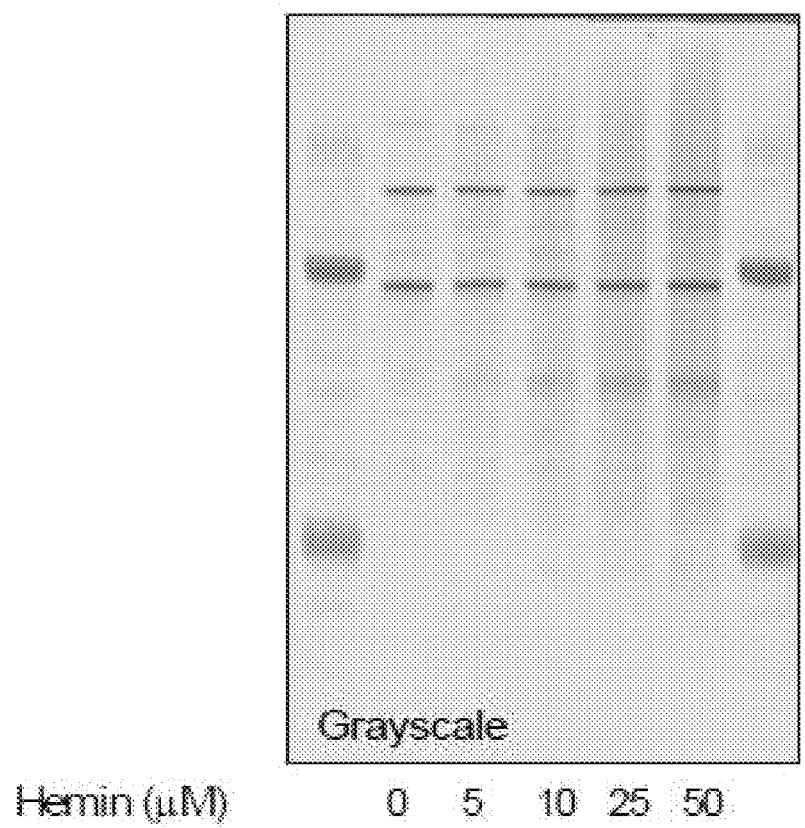
FIG. 22 shows an image of a Western blot probed with streptavidin-HRP for detection of lipid protein adducts in primary cortical neurons treated with hemin at concentrations of 0, 5, 10, 25, and 50 μM for 4 h.

NAC, trolox, and more selective ALOX5 inhibitors can inhibit the incorporation of ALOX5-derived reactive lipids into proteins. Electrophilic attack by ALOX5 products could alter cellular protein-mediated signaling to trigger cell death. Arachidonic acid (AA) tagged with biotin (Bt-AA) was used to monitor the formation of covalent protein adducts. To test whether hemin was sufficient to catalyze the formation of protein-reactive lipid species, primary neurons were treated with hemin at concentrations of 5 µM-50 µM for 4 h. Lipid protein adducts were detected by Western blots probed with Streptavidin-HRP. Bt-AA incorporation into protein increased with increasing concentrations of hemin, and significant lipid protein adducts were detected at 50 µM hemin. FIG. 22 shows an image of a Western blot probed with streptavidin-HRP for detection of lipid protein adducts in primary cortical neurons treated with hemin at concentrations of 0, 5, 10, 25, and 50 µM for 4 h. NAC treatment decreased hemin-induced ALOX5 gene expression and the generation of hemin-induced oxidized lipid species.

Figure 23:
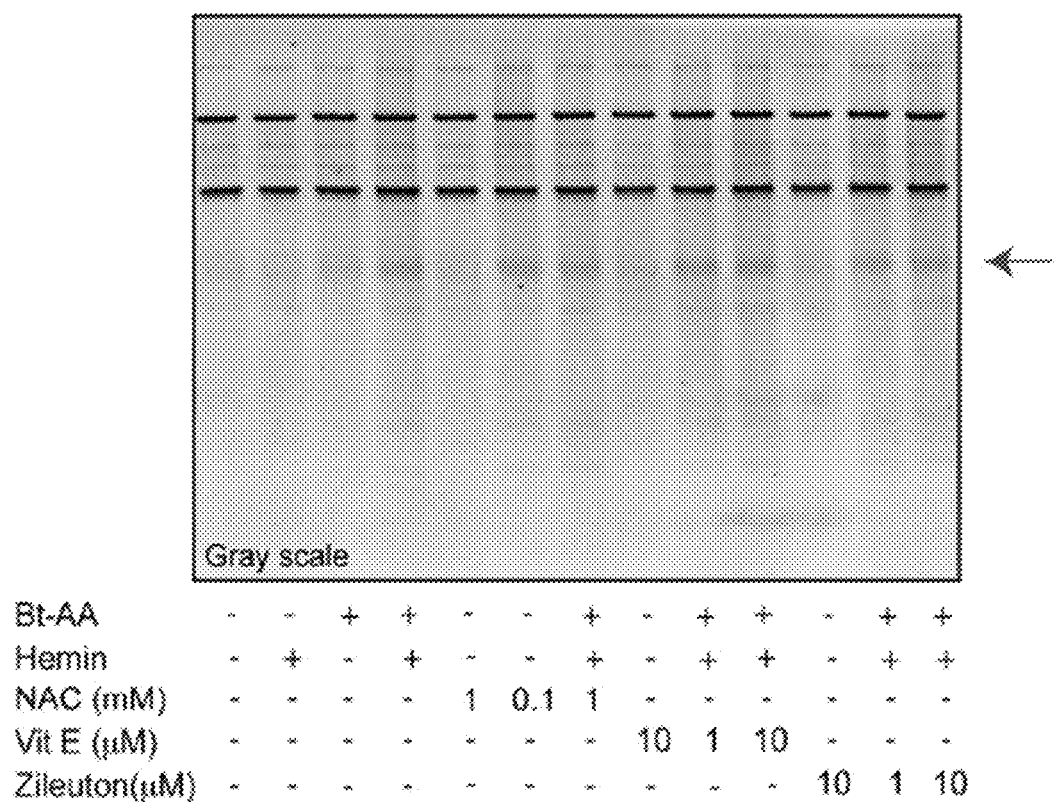
FIG. 23 shows an image of lipid protein adducts probed with streptavidin-HRP, demonstrating that NAC (1 mM), a-tocopherol (10 μM) and zileuton (10 μM) attenuated formation of hemin induced oxidized lipid protein adducts.

Non-protective doses of NAC (0.1 mM), vitamin E (1 µM), and zileuton (ALOX5 inhibitor, 1 µM) did not decrease AA-protein adduct formation. Protective doses of NAC (1 mM), vitamin E (10 µM), and zileuton (10 µM) decreased lipid protein adduct formation. FIG. 23 shows an image of lipid protein adducts probed with streptavidin-HRP, demonstrating that NAC (1 mM), α-tocopherol (10 µM) and zileuton (10 µM) attenuated formation of hemin-induced oxidized lipid protein adducts. The blot is representative from replicates of three experiments. The arrow indicates the decrease in lipid protein adduct formation. The data show that AA reacted with protein following the induction of ICH in vitro, and the interaction of proteins and reactive lipids was blocked by chemical ALOX5 inhibition, a non-selective lipid peroxidation inhibitor (vitamin E), or NAC.

Figure 24:
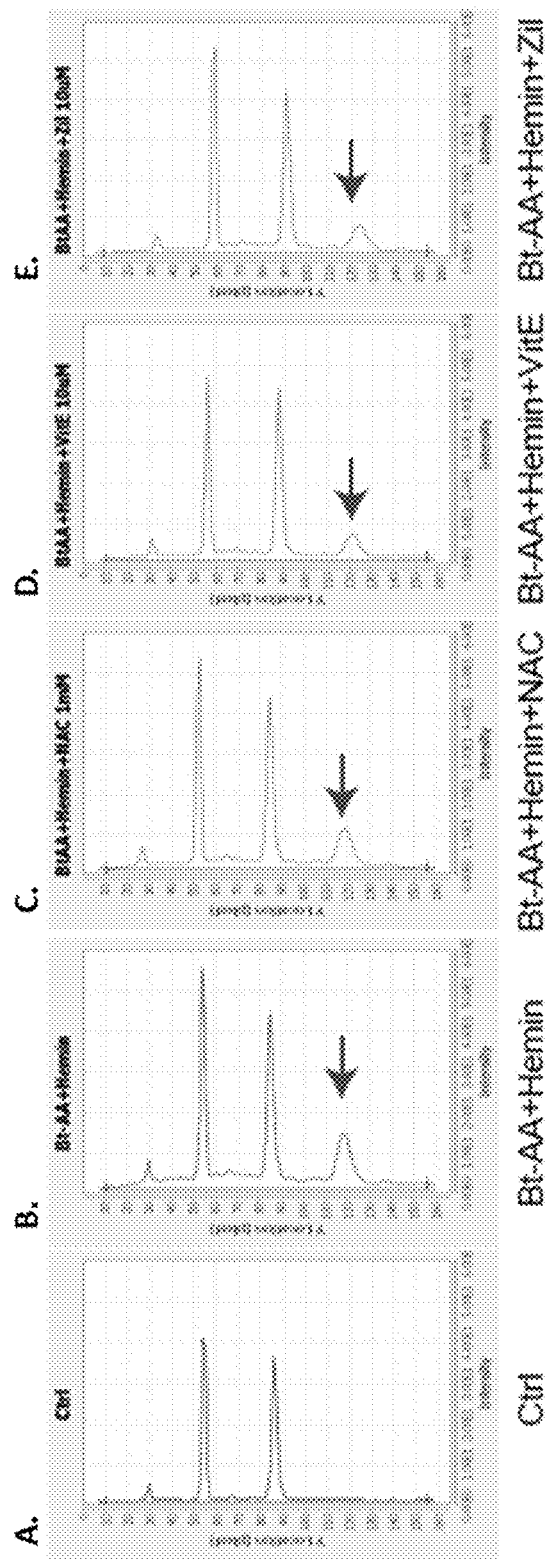
FIG. 24 shows quantification of the bands shown in FIG. 17, revealing a reduction in oxidized lipid protein adducts.

Quantification of the intensity of the experimental bands revealed that NAC, vitamin E, and zileuton inhibited lipid protein adduct formation. FIG. 24 shows quantification of the bands shown in FIG. 17, revealing a reduction in oxidized lipid protein adducts. The bands that were evident in the control wells were the endogenous biotin-containing carboxylases, and the bands confirmed equal gel loading between the groups. The results showed that the reactive lipids that were incorporated into proteins were abrogated by ALOX5 inhibitors (NAC or vitamin E).

The data were consistent with the ability of ALOX5 metabolites to incorporate into proteins to induce changes in signaling or dysfunction, and to induce cell death. The catalytic action of ALOX5 involved the formation of site-specific alkyl and lipid peroxyl radicals, generally not released from the enzyme and are inaccessible to lipid radical scavenging agents (e.g., vitamin E), which blocked access to the catalytic site of the enzyme. Low levels of the lipid radicals could exit the active site, which could initiate lipid peroxidation and be quenched by selective ALOX5 inhibitors or chain-breaking antioxidants, such as vitamin or NAC.

Example 8: NAC Efficacy Requires Increases in Glutathione; Protection by NAC is Mimicked by Glutathione S-Transferase A4

Figure 25:
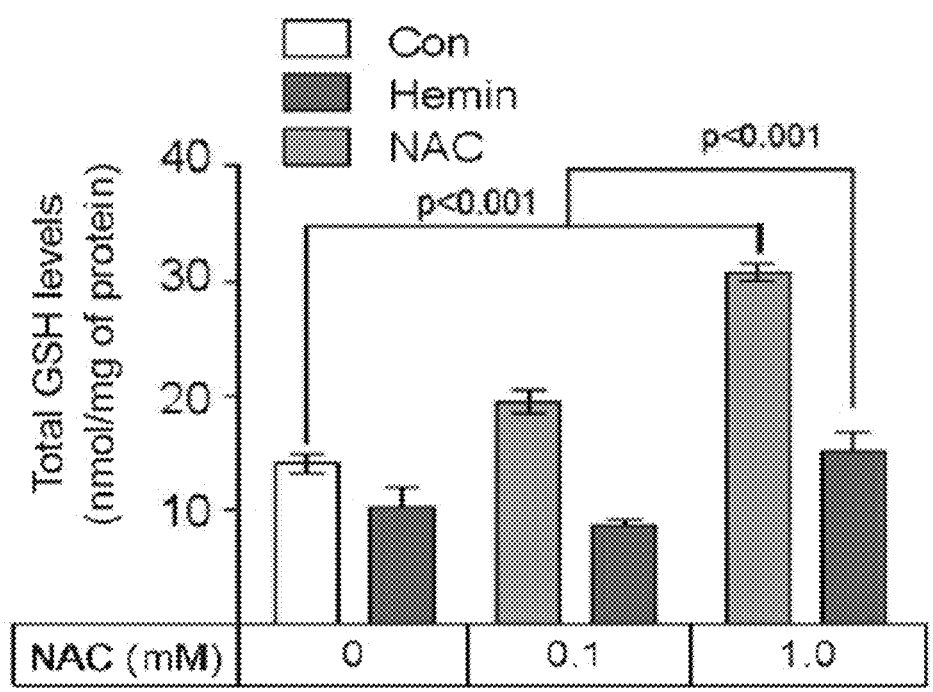
FIG. 25 shows the total glutathione (GSH) levels determined by HPLC analysis in neurons treated with 0 ("Con," vehicle), 0.1, or 1.0 mM NAC in the presence or absence of hemin.

Cysteine is the rate-limiting precursor for the synthesis of glutathione with γ-glutamylcysteine synthetase and glutathione synthetase. NAC undergoes hydrolysis to liberate cysteine, which is transported by the alanine-serine cysteine (ASC) system. To determine whether NAC-induced protection from heme requires glutathione, glutathione synthesis was inhibited using buthionine sulfoximine (BSO), a selective inhibitor of γ-glutamylcysteine synthetase, the rate limiting step in glutathione synthesis. The necessity of a NAC-induced increase in glutathione, and whether NAC-induced protection could be abrogated were evaluated. A reduction in glutathione levels was measured using HPLC. NAC dose-dependently increased the total glutathione levels in the presence or absence of hemin. In the presence of hemin, the absolute levels of glutathione were reduced. FIG. 25 shows the total glutathione levels determined by HPLC analysis in neurons treated with 0 ("Con," vehicle), 0.1, or 1.0 mM NAC in the presence or absence of hemin. The data show that NAC increased glutathione levels, and hemin blocked the increase of glutathione levels. Significance was determined by two-way ANOVA followed by Bonferroni's comparison test, from three independent experiments.

Figure 26:
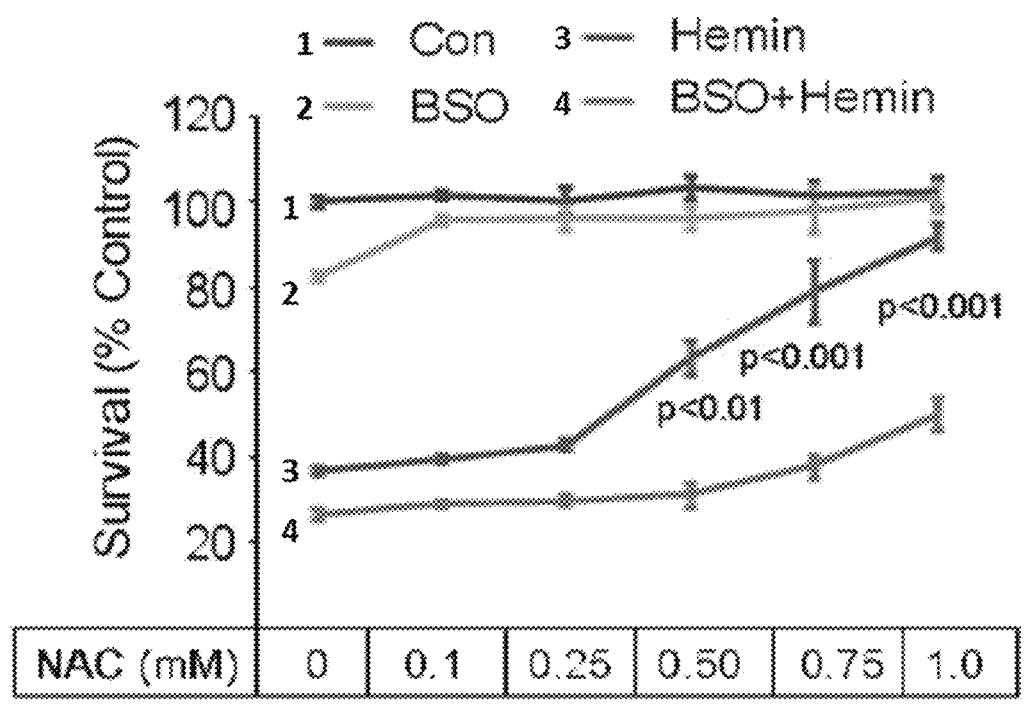
FIG. 26 shows the survival rates of neurons treated with 0 mM, 0.1 mM, 0.25 mM, 0.5 mM, 0.75 mM, or 1.0 mM NAC in the presence of vehicle (Con), hemin, buthionine sulphoximine (BSO) or BSO+hemin.

The ability of reduced total glutathione levels in blocking NAC-induced neuroprotection was evaluated. Cells were co-treated with NAC and BSO. Treatment of cells with BSO reversed NAC-induced protection, which was consistent with a model in which reduced glutathione nullifies reactive lipid species by interacting with glutathione-dependent enzymes. FIG. 26 shows the survival rates of neurons treated with 0 mM, 0.1 mM, 0.25 mM, 0.5 mM, 0.75 mM, or 1.0 mM NAC in the presence of vehicle (Con), hemin, BSO, or BSO+hemin. The data show that the pharmacological inhibition of γ-glutamylcysteine synthetase blocked the ability of NAC to prevent hemin toxicity in primary cortical neurons. Significance was determined by two-way ANOVA followed by Bonferroni's comparison test, from three independent experiments.

Increasing glutathione levels with (1) a membrane permeable form of glutathione (glutathione ethyl ester); (2) the cysteine prodrug L-oxothiazolidine decarboxylate; or (3) glial Nrf2 activator cystamine or nordihydroguaiaretic acid (NDGA), prevented hemin-induced death as effectively as NAC in vitro. The data suggest that NAC acted to increase glutathione to prevent ALOX5-induced ferroptosis.

TABLE 2 shows that strategies to increase glutathione levels in neurons or glia prevented hemin-induced ferroptosis. Glutathione ethyl ester, a membrane permeable form of glutathione; L-oxothiazolidine-4-carboxylate (OTC), a cysteine donor; Nrf2 activators cystamine and nordihydroguaiaretic acid (NGDA), which increases glutathione synthesis and glutathione-dependent detoxification enzymes, abrogated hemin-induced ferroptosis in primary cortical neurons as measured by an MTT assay. The effects of NAC were mimicked by other agents known to increase cysteine, such as OTC or glutathione ethyl ester. The Nrf2 activators (cystamine and NDGA), which induced glutathione synthesis and glutathione detoxification enzymes transcriptionally, also prevented hemin toxicity.

TABLE 2

| Pharmacological agents | Mechanism | $EC_{50}$ | % Viability |
| --- | --- | --- | --- |
| Vehicle | | | 100.00 |
| Hemin | | 100 μM | 50.14 |
| Glutathione ethyl ester | Glutathione prodrug | 2.5 mM | 83.70 |
| Oxothiazolidine-4-carboxylate | Cysteine donor | 2.5 mM | 99.40 |
| Cystamine | Nrf2 activator | 7.5 μM | 95.20 |
| Nordihydroguaiaretic acid | Nrf2 activator | 5.0 μM | 82.70 |

As cysteine is the rate-limiting precursor for glutathione synthesis, increasing cysteine with NAC or OTC increased glutathione levels. Activation of Nrf-2 increased transcriptional levels of cysteine transporters, glutathione synthesizing enzymes, and glutathione-related enzymes involved in suppression of lipid peroxidation.

Figure 27:
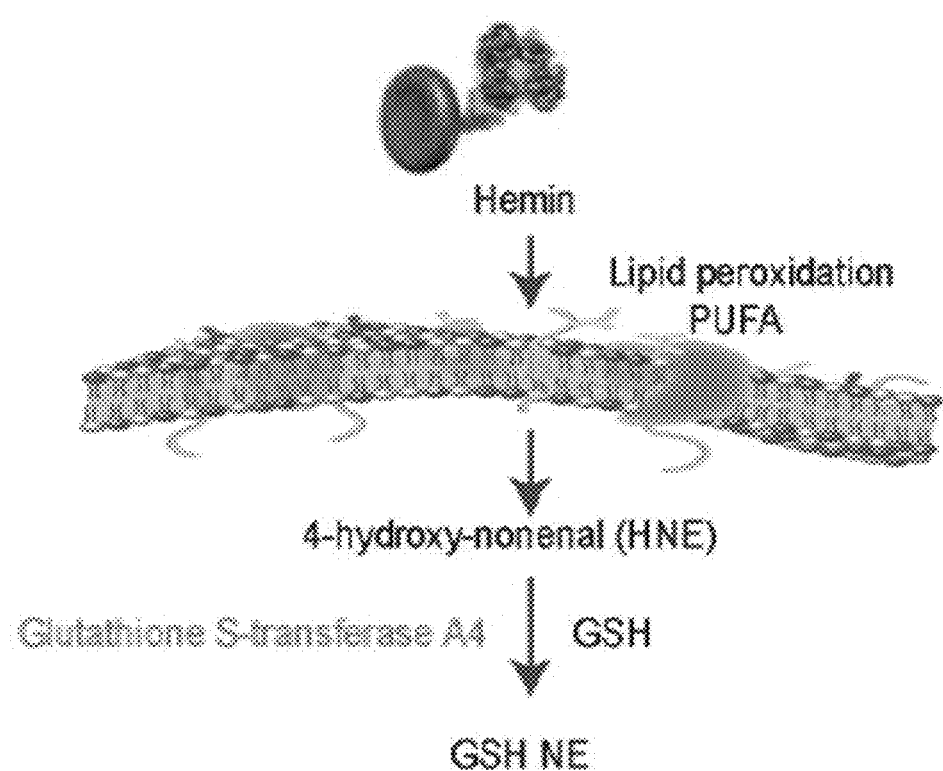
FIG. 27 illustrates the neutralization of oxidized lipid species by GSTA4.
Figure 28:
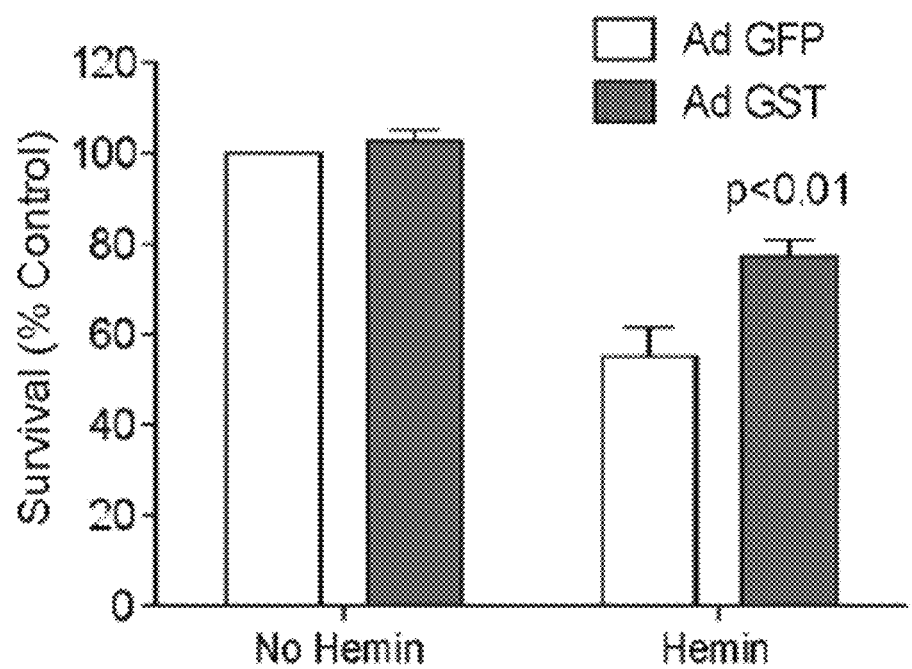
FIG. 28 shows the effects of adenovirus-mediated overexpression of GFP (Ad GFP) and GST (Ad GST) on survival of neurons with or without hemin treatment.

The requirement of increased glutathione levels for NAC efficacy was evaluated. The ability of the enzymatic lipid peroxidation inhibitor glutathione S-transferase $A_4$ ($GSTA_4$) to mimic NAC protection was also evaluated. FIG. 27 illustrates the neutralization of oxidized lipid species by $GSTA_4$. Adenoviral overexpression of $GSTA_4$ protected cells from hemin-induced toxicity. FIG. 28 shows the effects of adenovirus-mediated overexpression of GFP (Ad GFP) and GST (Ad GST) on the survival of neurons with or without hemin treatment. The data show that adenoviral overexpression of $GSTA_4$ protected cells from hemin-induced ferroptosis. Significance was determined by two-way ANOVA followed by Bonferroni's comparison test, from three independent experiments. The observations were consistent with a model in which reduced glutathione nullified reactive lipid species by interacting with glutathione-dependent enzymes. Glutathione prodrugs and enzymatic inhibitors of oxidized lipid species protected primary cortical neurons from hemin toxicity. NAC protection against hemin toxicity in vitro was dependent on glutathione levels or flux, indicating that direct scavenging or reactions with electrophiles were not required for NAC's beneficial effects.

Figure 29:
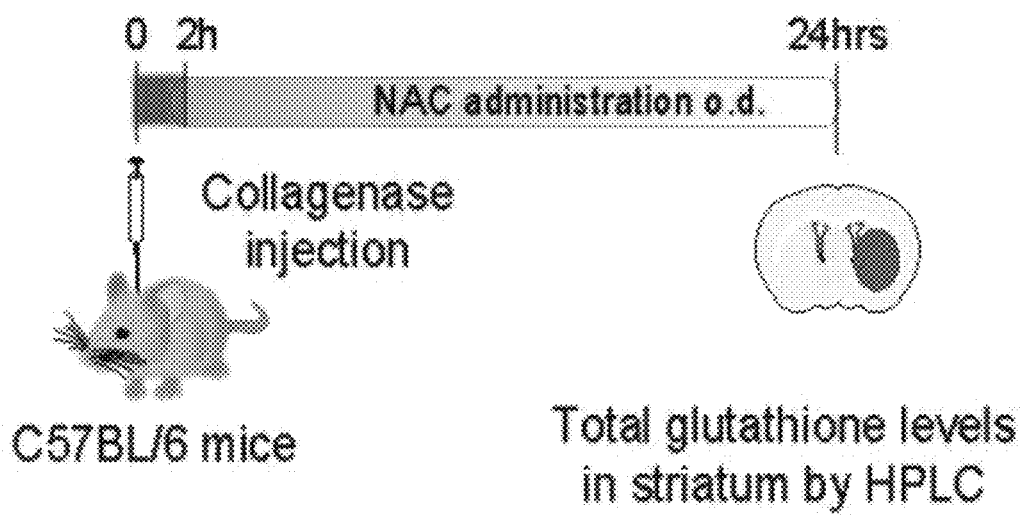
FIG. 29 illustrates an experimental design to study the effect of NAC on total glutathione levels in the striatum of a collagenase infusion mouse model of ICH.
Figure 30:
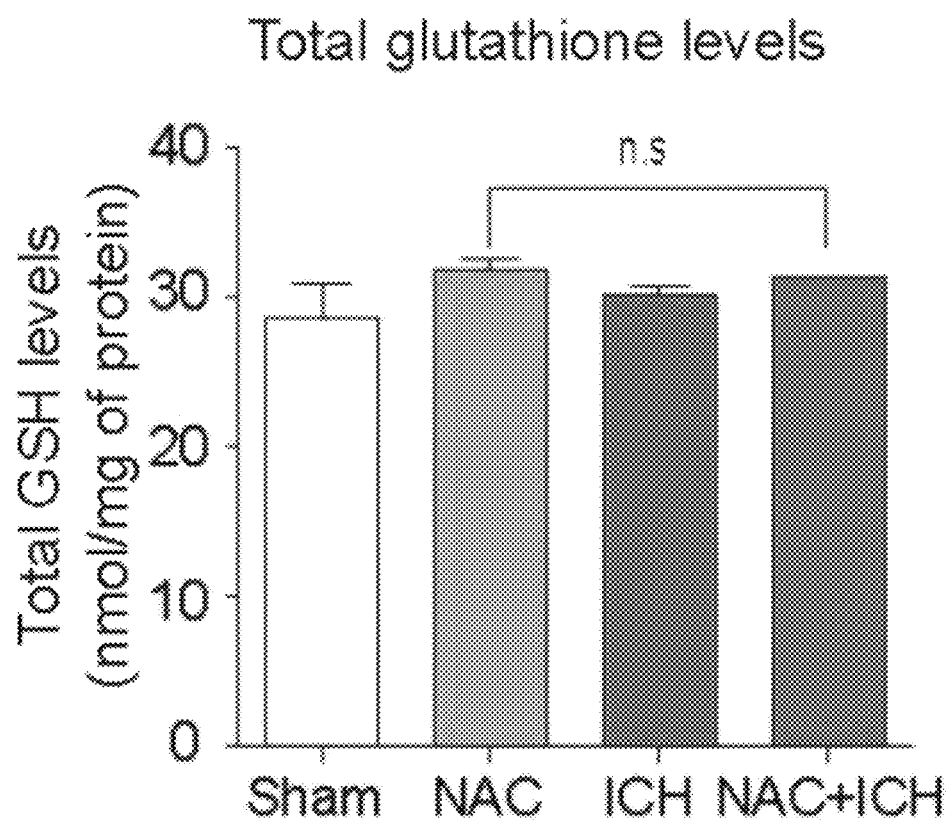
FIG. 30 shows total glutathione levels by HPLC analysis in the striatum of sham injected mice with or without NAC treatment, and in collagenase-infused ICH mice with or without NAC treatment.

Total glutathione levels were unchanged after NAC treatment in ICH mice. The specific action of ATF4-regulated Chac1 a γ-glutamyl cyclotransferases to degrade GSH was decreased after NAC treatment. FIG. 29 illustrates an experimental design to study the effect of NAC on total glutathione levels in the striatum of a collagenase infusion mouse model of ICH. FIG. 30 shows total glutathione levels by HPLC analysis in the striatum of sham injected mice with or without NAC treatment, and in collagenase-infused ICH mice with or without NAC treatment. The data show that total glutathione levels in NAC-treated brains were unchanged.

Figure 31:
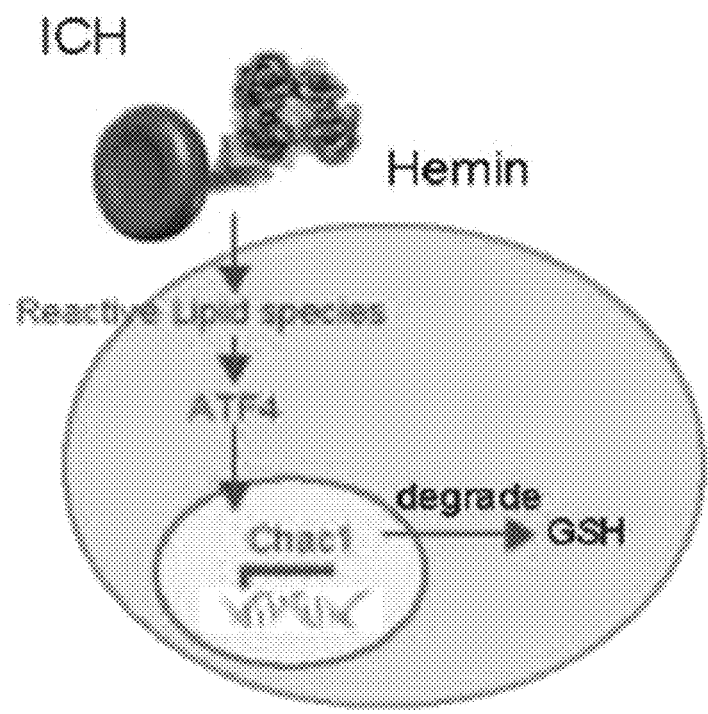
FIG. 31 shows illustrates that ICH-induced ATF4 dependent Chac1 degraded glutathione to 5-oxoproline.
Figure 32:
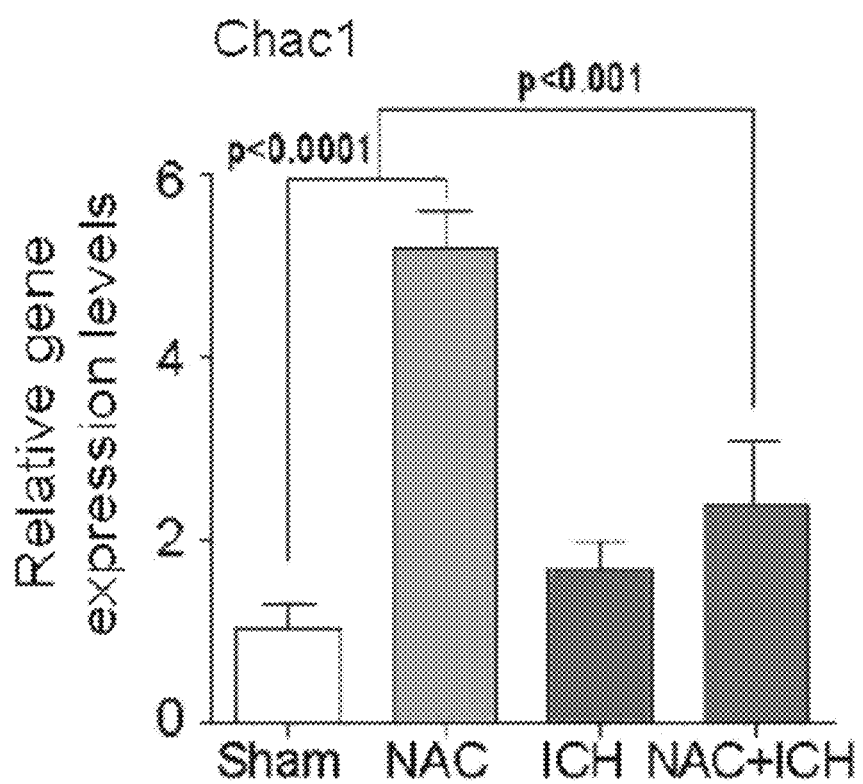
FIG. 32 shows the relative Chac1 gene expression levels as measured by quantitative RT-PCR in neurons of sham injected mice with or without NAC treatment, and of collagenase-infused ICH mice with or without NAC treatment.

FIG. 31 illustrates that ICH-induced ATF4 dependent Chac1 degraded glutathione to 5-oxoproline. FIG. 32 shows the relative Chac1 gene expression levels as measured by quantitative RT-PCR in neurons of sham-injected mice with or without NAC treatment, and of collagenase-infused ICH mice with or without NAC treatment. The data show that ATF4-dependent Chac1 was significantly induced by NAC. ATF4-dependent Chac1 induction was significantly reduced in ICH mice. The data demonstrate that NAC reduced nuclear 5-lipoxigenase accumulation in ICH or hemin-treated neurons.

Figure 33:
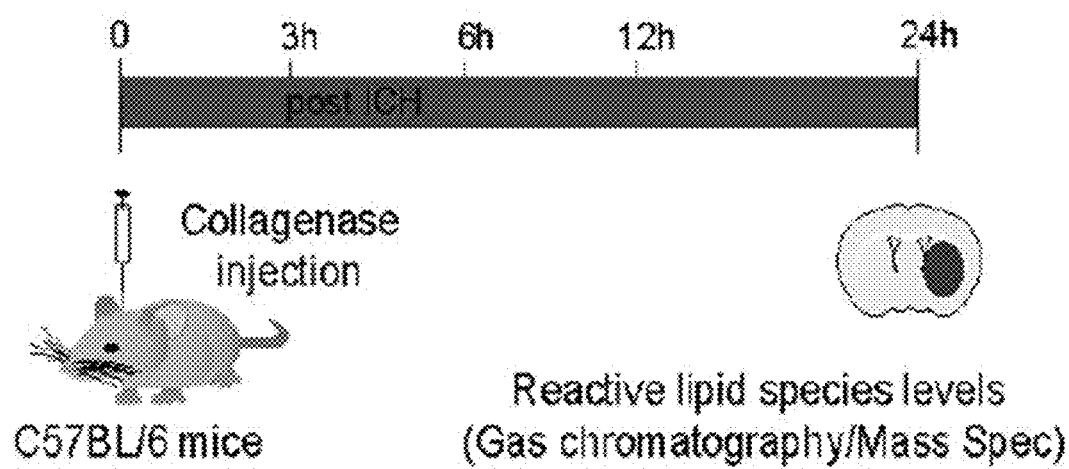
FIG. 33 illustrates an experimental design for analyzing eicosanoid levels post-ICH in mice.

Example 9: Targeted Lipidomics Identified Prosurvival Prostaglandin PGE2 as Providing Synergy with NAC to Treat ICH Expected increases of ALOX5 metabolites in rats following ICH were observed in vivo. A targeted lipidomic approach was used to address which lipid species are altered in ICH, and to analyze the eicosanoid levels at different time intervals in ICH brains using GC/MS analysis. FIG. 33 illustrates an experimental design for analyzing eicosanoid levels post-ICH in mice.

Figure 34:
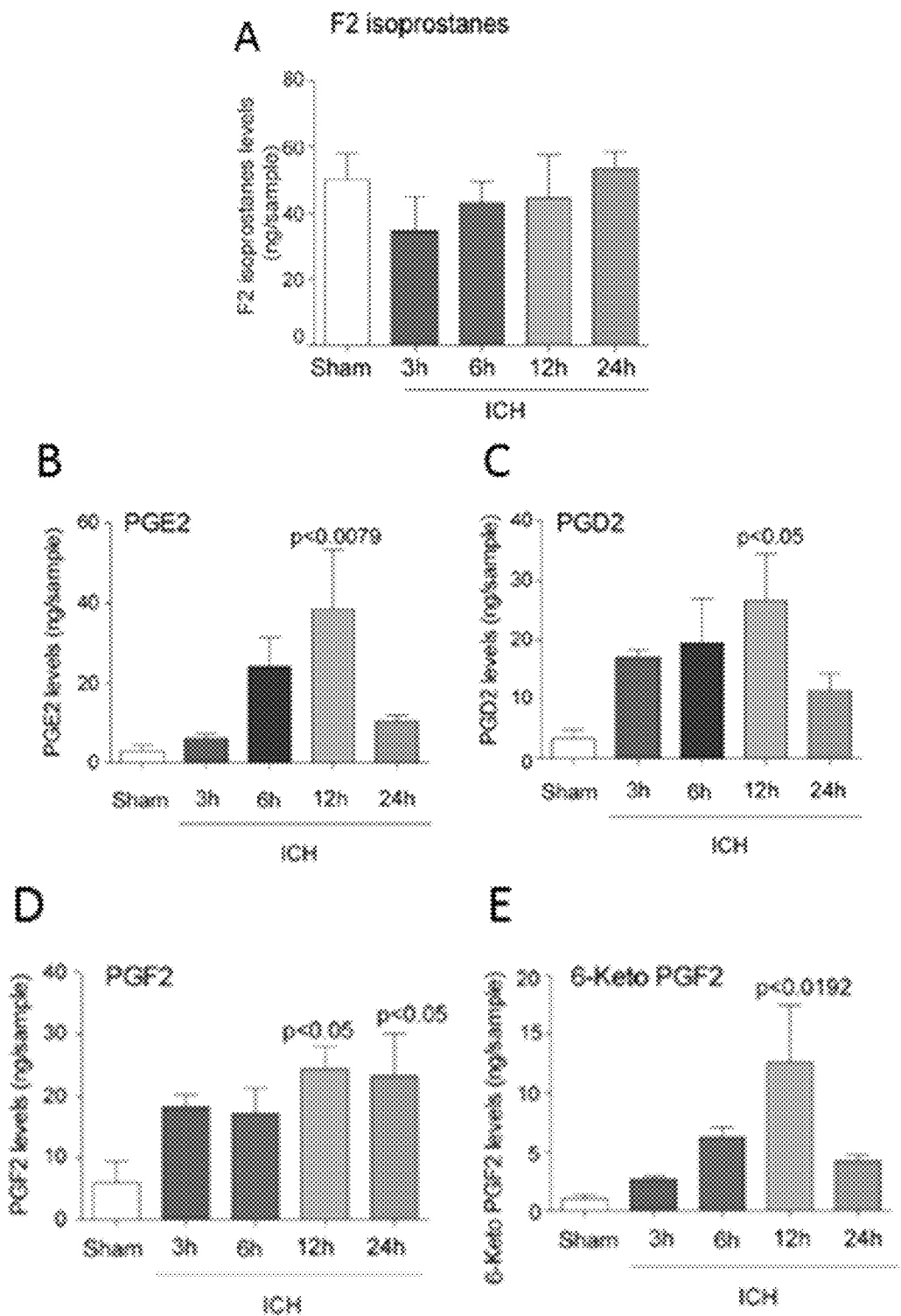
FIG. 34 PANEL A shows $F_2$ isoprostane levels in sham-injected mice and in collagenase-infused ICH mice over time following collagenase injection.

The GC/MS analysis from rats revealed that ICH-induced COX-dependent lipid species. ICH induced the cyclooxygenase-dependent lipid species PGE2 significantly at 12 h. FIG. 34 PANEL A shows $F_2$ isoprostane levels in sham-injected mice and in collagenase-infused ICH mice over time following collagenase injection. The data show that $F_2$ isoprostanes levels were unchanged. FIG. 34 PANEL B shows prostaglandin $E_2$ ($PGE_2$) levels as determined by GC/MS analysis in sham-injected mice and in collagenase-infused ICH mice over time following collagenase injection. A significant increase in prostaglandin $PGE_2$ levels was observed 12 h post-ICH. FIG. 34 PANEL C shows prostaglandin D2 ($PGD_2$) levels as determined by GC/MS analysis in sham-injected mice and in collagenase-infused ICH mice over time following collagenase injection. An increase in $PGD_2$ levels was observed 12 h post-ICH. FIG. 34 PANEL D shows prostaglandin F2 ($PGF_2$) levels as determined by GC/MS analysis in sham-injected mice and in collagenase-infused ICH mice over time following collagenase injection. An increase in $PGF_2$ levels was observed 12 h post-ICH.

FIG. 34 PANEL E shows 6-keto-prostaglandin $F_2$ (6-keto $PGF_2$) levels as determined by GC/MS analysis in sham-injected mice and in collagenase-infused ICH mice over time following collagenase injection. A significant increase in prostaglandin 6-keto-$PGF_2$ levels was observed 12 h post-ICH. Data from sham control brains from each time point was pooled for the analysis. Significance was determined by one-way ANOVA and Dunnet's multiple comparison test. All graphs are mean±SEM.

The data suggest that AA metabolites downstream of ALOX5 and COX increased following ICH, whereas the non-enzymatic lipid species $F_2$ isoprostane levels were not increased following ICH. The results were consistent with the observation that COX-2 and downstream metabolic enzymes are induced following ICH. COX inhibitors, which would be expected to diminish $PEG_2$, did not worsen hemin0induced death in mixed neuronal-glia cultures (data not shown). The data demonstrate that a cell type other than neurons or glia (e.g., microglia or macrophages) may be relevant for producing $PEG_2$ in ICH, which were not present in the in vitro cultures.

The ability of the $PGE_2$-mediated adaptive response to synergize with NAC protection in vitro was evaluated. Secondary injury in ICH was modeled using exogenous exposure of cultured neurons to hemin or heme. Exposure to either hemin or heme led to cell death of neurons within 24 hours. Neurons were treated with a sub-threshold dose of 16,16-dimethyl $PGE_2$ ($dmPGE_2$, a long-acting analogue of $PGE_2$) (10 µM) and with different concentrations of NAC with hemin. Cell survival was assessed using MTT. Treatment with NAC or $dmPGE_2$ dose-dependently abrogated hemin-induced toxicity. Despite modest protection from hemin-induced ferroptosis by $dmPGE_2$ in cortical neurons, treatment of NAC (100 µM) and $dmPGE_2$ (10 µM) provided synergistic protection.

Figure 35:
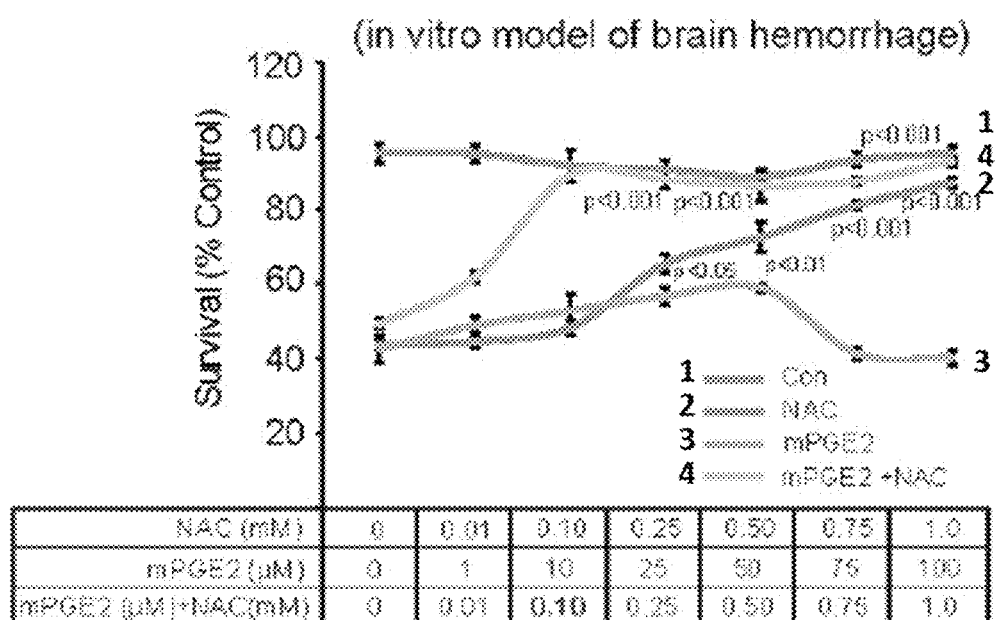
FIG. 35 shows survival rates of primary cortical neurons treated with vehicle (Con) or with various concentrations of NAC, $mPGE_2$, or $mPGE_2$+NAC.

FIG. 35 shows survival rates of primary cortical neurons treated with vehicle (Con) or with various concentrations of NAC, $mPGE_2$, or $mPGE_2$+NAC. The data show that NAC+$PGE_2$ provided synergy against hemin-induced toxicity in primary cortical neurons. The results showed that combinatorial treatment of $dmPGE_2$ and NAC reduced the concentration of NAC required for protection by 10-fold in vitro.

Figure 36:
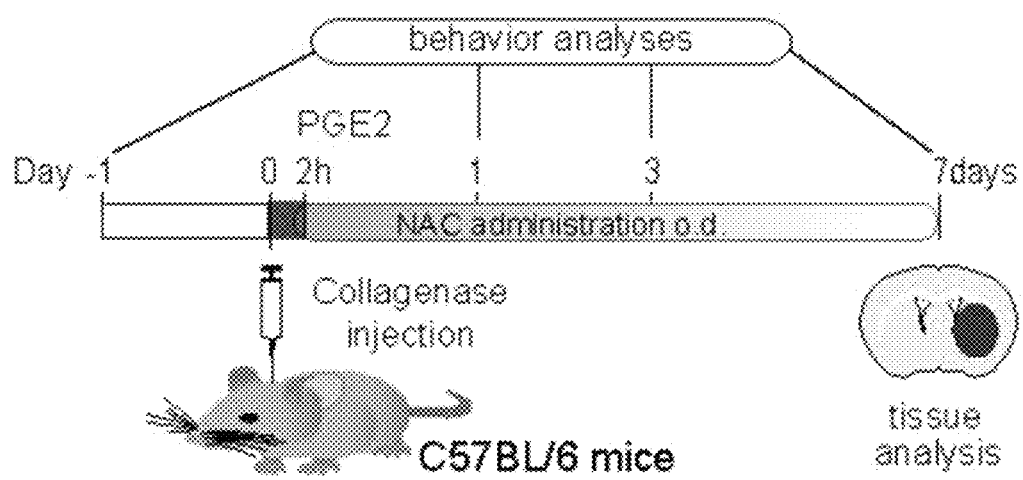
FIG. 36 illustrates a schematic of an experimental design for combinatorial delivery of NAC and $PGE_2$ after ICH.

The ability of NAC and $PGE_2$ to provide a synergistic effect on functional recovery after ICH was evaluated in vivo. NAC (40 mg/kg; i.p., a dose ineffective in mice and rats) and $dmPGE_2$ (10 µM; ICV) were delivered 2 h post-injury. NAC 40 mg/kg was then administered intraperitoneally once daily for seven days. FIG. 36 illustrates a schematic of an experimental design for combinatorial delivery of NAC and $PGE_2$ after ICH.

Figure 37:
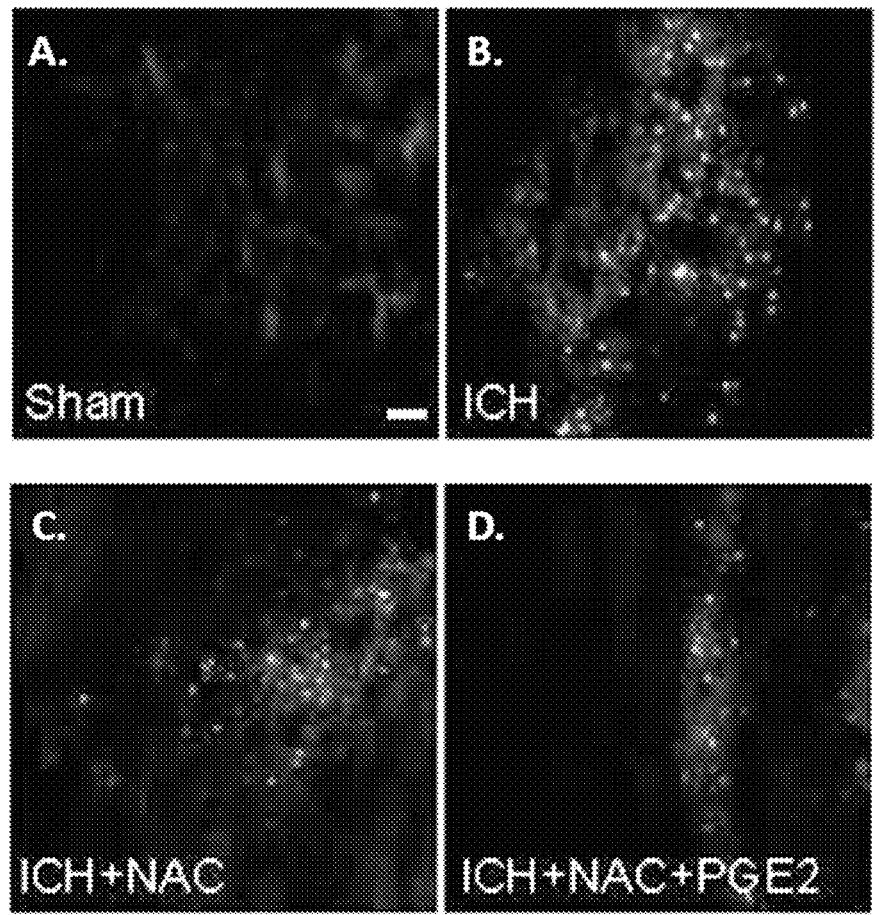
FIG. 37 shows photographs showing Fluoro-Jade® staining of neurons in sham injected mice, untreated collagenase-injected ICH mice, and collagenase-injected ICH mice treated with NAC or NAC+$PGE_2$.
Figure 38:
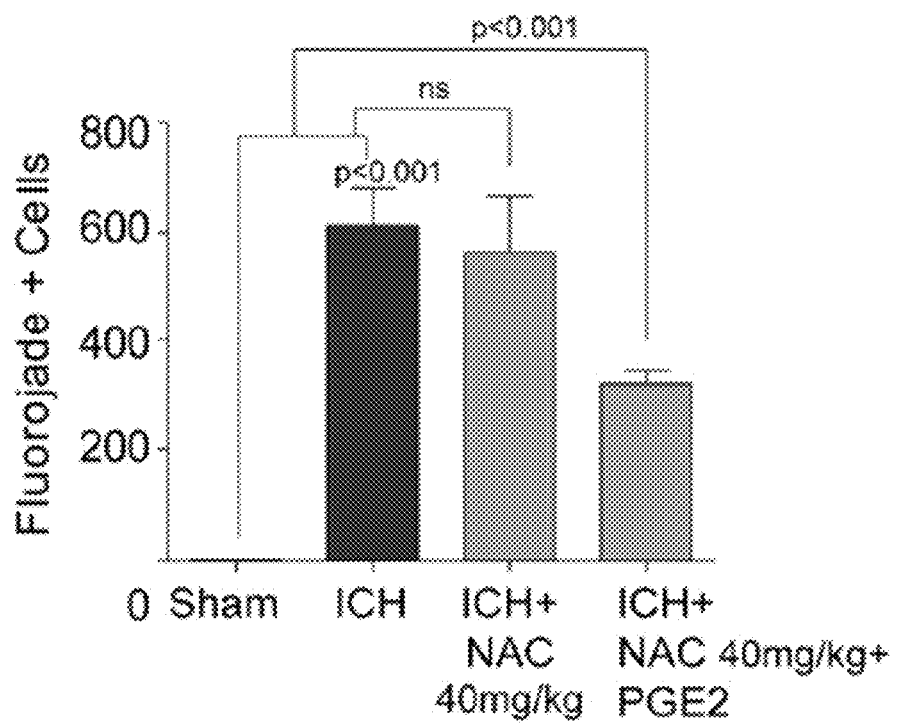
FIG. 38 quantifies the Fluoro-Jade® staining of neurons in sham injected mice, untreated collagenase-injected ICH mice, and collagenase-injected ICH mice treated with NAC or NAC+$PGE_2$.

The combination treatment of neurons with low dose NAC and $dmPGE_2$ reduced neuronal degeneration as monitored by Fluoro-Jade® staining in the perihematomal regions of the mouse brain after ICH. FIG. 37 shows photographs showing Fluoro-Jade® staining of neurons in sham injected mice, untreated collagenase-injected ICH mice, and collagenase-injected ICH mice treated with NAC or NAC+$PGE_2$. The data show that the combination of low doses of NAC and $PGE_2$ reduced neuronal degeneration in the perihematomal regions of the mouse brain after ICH. NAC or $dmPGE_2$ alone had no significant effect. FIG. 38 quantifies the Fluoro-Jade® staining of neurons in sham injected mice, untreated collagenase-injected ICH mice, and collagenase-injected ICH mice treated with NAC or NAC+$PGE_2$.

Figure 39:
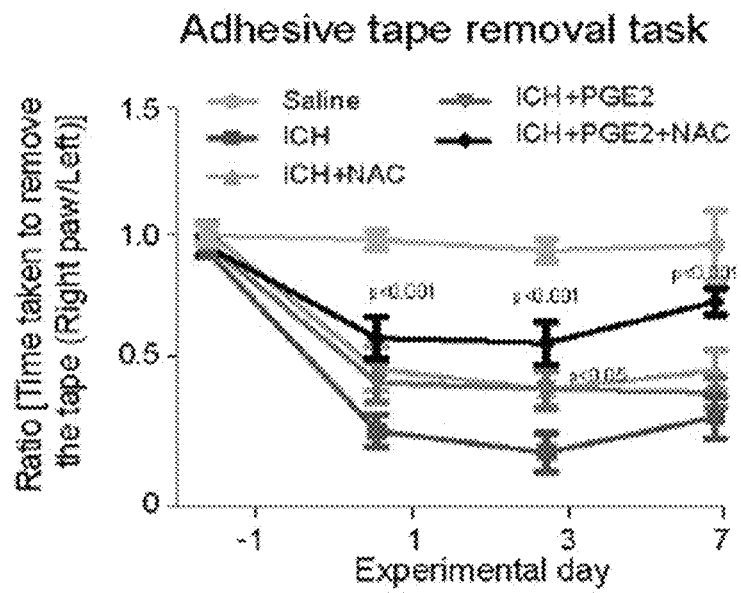
FIG. 39 PANEL A shows behavioral analysis results for the corner task in saline-injected mice, untreated collagenase-injected ICH mice, and collagenase-injected ICH mice treated with NAC, $PGE_2$, or NAC+$PGE_2$.
Figure 39:
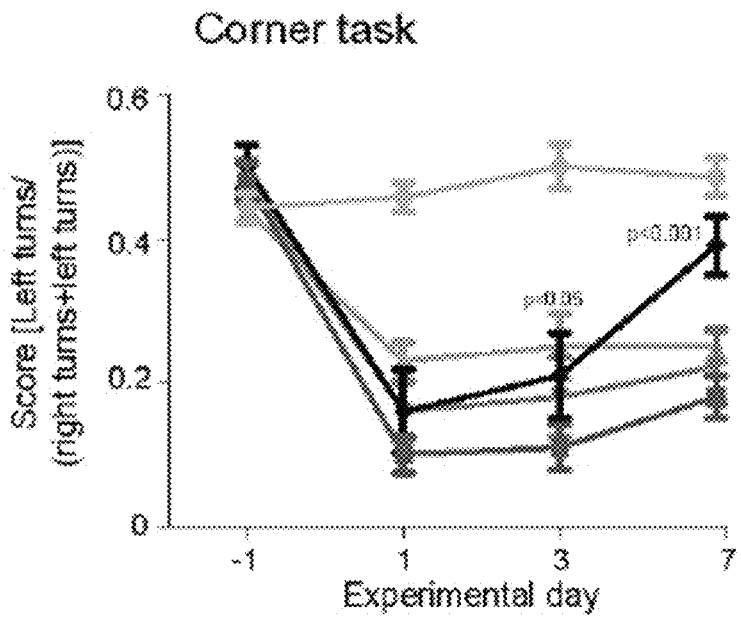

Behavioral studies following ICH showed that the combination of NAC+$dmPGE_2$ significantly improved behavioral deficits induced by ICH. Behavioral analysis using the corner task (spatial neglect) and adhesive tape removal task (sensory neglect) was performed on days 1, 3 and 7 after ICH. FIG. 39 PANEL A shows behavioral analysis results for the corner task in saline-injected mice, untreated collagenase-injected ICH mice, and collagenase-injected ICH mice treated with NAC, PGE2, or NAC+PGE2. FIG. 39 PANEL B shows behavioral analysis results for the adhesive tape removal task in saline-injected mice, untreated collagenase-injected ICH mice, and collagenase-injected ICH mice treated with NAC, PGE2, or NAC+PGE2.

The combination of NAC+$PGE_2$ improved spatial neglect (corner task) and sensory neglect (adhesive tape removal task) behavioral deficits induced by ICH. Treatment with NAC or $PGE_2$ alone had no effect on spatial neglect (corner task) and sensory neglect (adhesive tape removal task) behavioral deficits induced by ICH. Observations from the behavioral analysis show that targeted lipidomics in an ICH context has identified that $PGE_2$ provides a synergistic protective effect with NAC in both an in vitro hemin model and an in vivo collagenase model of ICH. These findings demonstrate that combinatorial administration of NAC and $PGE_2$ can synergistically protect the brain, and reduce the concentration of NAC required to improve functional recovery following ICH in mice.

ALOX5 inhibitors did not synergize with $PEG_2$ (data not shown). NAC may alter $PEG_2$ signaling directly rather than via its effects on ALOX5-derived products.

Example 10: Intranasal Administration of NAC to Treat CNS Conditions

A college athlete suffers a concussion and is diagnosed with a concussion using standard evaluation, such as CogScreen, ImPACT v2, or SCAT3. The athlete is given a dose of NAC of 1 mg/kg-10 mg/kg intranasally three hours after the concussion, and a similar dose on each of the following fourteen days. The athlete's scores on the evaluations are monitored.

Example 11: Intranasal Administration of NAC and PGE$_2$ to Treat CNS Conditions A college athlete suffers a concussion and is diagnosed with a concussion using standard evaluation, such as CogScreen, ImPACT v2, or SCAT3. The athlete is given a dose of NAC of 1 mg/kg-10 mg/kg and PGE$_2$ dose intranasally three hours after the concussion, and a similar dose on each of the following fourteen days. The athlete's scores on the evaluations are monitored.

EMBODIMENTS

The following non-limiting embodiments provide illustrative examples of the invention, but do not limit the scope of the invention.

Embodiment 1. A method of treating a central nervous system condition comprising administering to a subject in need thereof a therapeutically-effective amount of a 5-lipoxygenase activating protein (FLAP) inhibitor.

Embodiment 2. The method of embodiment 1, wherein the FLAP inhibitor is N-acetylcysteine or a pharmaceutically-acceptable salt thereof.

Embodiment 3. The method of embodiment 1, wherein the FLAP inhibitor is an N-acetylcysteine prodrug or a pharmaceutically-acceptable salt thereof.

Embodiment 4. The method of embodiment 1, wherein the FLAP inhibitor is N-acetylcysteine amide or a pharmaceutically-acceptable salt thereof.

Embodiment 5. The method of embodiment 1, wherein the FLAP inhibitor is cystamine or a pharmaceutically-acceptable salt thereof.

Embodiment 6. The method of embodiment 1, wherein the FLAP inhibitor is nordihydroguaiaretic acid or a pharmaceutically-acceptable salt thereof.

Embodiment 7. The method of any one of embodiments 1-6, wherein the administering is intranasal.

Embodiment 8. The method of any one of embodiments 1-7, wherein the central nervous system condition is a brain injury.

Embodiment 9. The method of any one of embodiments 1-8, wherein the brain injury is a stroke.

Embodiment 10. The method of any one of embodiments 1-9, wherein the stroke is intracerebral hemorrhagic stroke.

Embodiment 11. The method of any one of embodiments 1-8, wherein the brain injury is subarachnoid hemorrhage.

Embodiment 12. The method of any one of embodiments 1-7, wherein the central nervous system condition is a neuropsychiatric disorder.

Embodiment 13. The method of any one of embodiments 1-7 or 12, wherein the neuropsychiatric disorder is schizophrenia.

Embodiment 14. The method of any one of embodiments 1-7 or 12, wherein the neuropsychiatric disorder is bipolar disorder.

Embodiment 15. The method of any one of embodiments 1-7 or 12, wherein the neuropsychiatric disorder is depression.

Embodiment 16. The method of any one of embodiments 1-7, wherein the central nervous system condition is spinal cord injury.

Embodiment 17. The method of any one of embodiments 1-7, wherein the central nervous system condition is associated with oxidative stress.

Embodiment 18. The method of any one of embodiments 1-7, wherein the central nervous system condition is associated with endoplasmic reticulum stress.

Embodiment 19. The method of any one of embodiments 1-7, wherein the central nervous system condition is associated with excitotoxic stress.

Embodiment 20. The method of any one of embodiments 1-19, wherein the therapeutically-effective amount is about 1 mg/kg to about 10 mg/kg.

Embodiment 21. The method of any one of embodiments 1-20, wherein the subject is human.

What is claimed is:

1. A method of treating a Parkinson's disease, the method comprising intranasally administering to a subject in need thereof about 100 mg to about 350 mg of N-acetyl cysteine (NAC) as an intranasal spray, wherein the administering is to a brain of the subject through a nasal cavity of the subject.

2. The method of claim 1, wherein the subject is human.

3. The method of claim 1, wherein the NAC is administered as a powder formulation.

4. The method of claim 3, wherein the powder formulation further comprises a pharmaceutically acceptable excipient.

5. The method of claim 4, wherein the pharmaceutically acceptable excipient is a monosaccharide.

6. The method of claim 5, wherein the monosaccharide is glucose.

7. The method of claim 4, wherein the pharmaceutically acceptable excipient is a disaccharide.

8. The method of claim 7, wherein the disaccharide is lactose.

9. The method of claim 4, wherein the pharmaceutically acceptable excipient is an oligosaccharide.

10. The method of claim 9, wherein the oligosaccharide is dextrane.

11. The method of claim 4, wherein the pharmaceutically acceptable excipient is a salt.

12. The method of claim 11, wherein the salt is sodium chloride.

13. The method of claim 11, wherein the salt is calcium carbonate.

14. The method of claim 1, wherein the NAC is administered as a sprayable powder.

15. The method of claim 1, wherein the NAC is administered as a dry powder.

16. The method of claim 1, wherein the NAC is administered as a liquid composition.

17. The method of claim 16, wherein the liquid composition comprises liposomes, micelles, or nanoparticles.

18. The method of claim 1, wherein the NAC is administered as any of a liquid, a powder, a gel, a nanosuspension, a nanoparticle, a microgel, a aqueous, an oily suspension, an emulsion, or a combination thereof.

19. A method of treating a Parkinson's disease condition, the method comprising intranasally administering to a subject in need thereof about 100 mg to about 350 mg of N-acetyl cysteine (NAC) using a nasal sprayer, wherein the administering is to a brain of the subject through a nasal cavity of the subject.

20. The method of claim 19, wherein the nasal sprayer is any of a multi-dose metered-dose spray pump, single-dose spray pump, a duo-dose spray pump, and a bidirectional multi-dose spray pump.

21. The method of claim 19, wherein the nasal sprayer comprises a pressurized aerosol container.

22. The method of claim 19, wherein the nasal sprayer is a mechanical powder spray device.

* * * * *